United States Patent
Gillis et al.

(10) Patent No.: US 6,821,731 B2
(45) Date of Patent: Nov. 23, 2004

(54) EXPRESSION ANALYSIS OF FKBP NUCLEIC ACIDS AND POLYPEPTIDES USEFUL IN THE DIAGNOSIS OF PROSTATE CANCER

(75) Inventors: Kimberly A. Gillis, Swampscott, MA (US); Yixian Zhang, Pearl River, NY (US)

(73) Assignee: Wyeth, Madison, NJ (US)

(*) Notice: Subject to any disclaimer, the term of this patent is extended or adjusted under 35 U.S.C. 154(b) by 0 days.

(21) Appl. No.: 09/997,423

(22) Filed: Nov. 28, 2001

(65) Prior Publication Data

US 2002/0168650 A1 Nov. 14, 2002

Related U.S. Application Data

(60) Provisional application No. 60/253,539, filed on Nov. 28, 2000.

(51) Int. Cl.[7] ................. C12Q 1/68; G01N 33/53; C12P 19/34; C07H 21/04; C07K 14/47
(52) U.S. Cl. ................. 435/6; 435/7.1; 435/91.2; 435/91.5; 435/91.51; 536/23.5; 530/350
(58) Field of Search .............. 435/6, 7.1, 91.2, 435/91.5, 91.51; 536/23.5; 530/350

(56) References Cited

U.S. PATENT DOCUMENTS

| 5,030,559 A | 7/1991 | Nicolson et al. |
| 5,118,611 A | 6/1992 | Smith et al. |
| 5,362,718 A | 11/1994 | Skotnicki et al. |

(List continued on next page.)

FOREIGN PATENT DOCUMENTS

| EP | 0 698 215 B1 | 7/1998 |
| EP | 0 939 084 A1 | 9/1999 |
| EP | 0 974 652 A1 | 1/2000 |
| EP | 0 648 126 B1 | 2/2000 |
| WO | WO 97/08318 | 3/1997 |
| WO | WO 97/33909 | 9/1997 |
| WO | WO 98/37093 | 8/1998 |
| WO | WO 98/37418 | 8/1998 |
| WO | WO 99/18210 | 4/1999 |
| WO | WO 99/37811 | 7/1999 |
| WO | WO 00/04149 | 1/2000 |
| WO | WO 00/14234 | 3/2000 |
| WO | WO 00/18961 | 4/2000 |
| WO | WO 00/55174 | 9/2000 |
| WO | WO 00/55350 | 9/2000 |
| WO | WO 02/31209 | 4/2002 |

OTHER PUBLICATIONS

Database Genbank Online, www.ncbi.nlm.nih.gov, Database Accession No. NM_004117, Apr. 5, 2003.

Zhu et al., "Silymarin inhibits function of the androgen receptor by reducing nuclear localization of the receptor in the human prostate cancer cell line LNCaP," *Carcinogenesis*, vol. 22, No. 9, Sep. 2001, pp 1399–1402.

Chung et al., "Effects of docosahexaenoic acid and eicosapentaenoic acid on androgen–mediated cell growth and gene expression in LNCaP prostate cancer cells," *Carcinogenesis*, vol. 22, No. 8, Aug. 2001, pp 1201.

Amler et al., "Dysregulated Expression of Androgen–responsive and Nonresponsive Genes in the Androgen–independent Prostate Cancer Xenograft Model CWR22–R," *Cancer Research*, vol. 60, No. 21, Nov. 1, 2000, pp 6134, 6139–6140.

(List continued on next page.)

*Primary Examiner*—Diana B. Johannsen
(74) *Attorney, Agent, or Firm*—Thomas J. Engellenner; Deborah A. Miller; Nutter McClennen & Fish LLP

(57) ABSTRACT

The invention relates to compositions, kits, and methods for detecting, characterizing, preventing, and treating prostate cancer. FKBP markers are provided, wherein changes in the levels of expression of one or more of the FKBP markers is correlated with the presence of prostate cancer.

17 Claims, 5 Drawing Sheets

U.S. PATENT DOCUMENTS

| | | |
|---|---|---|
| 5,629,007 A | 5/1997 | Audia et al. |
| 5,635,197 A | 6/1997 | Audia et al. |
| 5,674,682 A | 10/1997 | Croce et al. |
| 5,688,658 A | 11/1997 | Diamandis |
| 5,723,302 A | 3/1998 | Diamandis |
| 5,763,202 A | 6/1998 | Horoszewicz |
| 5,801,197 A | 9/1998 | Steiner et al. |
| 5,843,994 A | 12/1998 | Samid |
| 5,854,206 A | 12/1998 | Twardzik et al. |
| 5,856,112 A | 1/1999 | Marley et al. |
| 5,859,031 A | 1/1999 | Hamilton et al. |
| 5,861,248 A | 1/1999 | Russell et al. |
| 5,882,864 A | 3/1999 | An et al. |
| 5,912,253 A | 6/1999 | Cottens et al. |
| 5,939,258 A | 8/1999 | Croce et al. |
| 5,945,522 A | 8/1999 | Cohen et al. |
| 5,968,802 A | 10/1999 | Wang et al. |
| 5,972,615 A | 10/1999 | An et al. |
| 5,976,794 A | 11/1999 | Katz et al. |
| 5,976,838 A | 11/1999 | Jacobs et al. |
| 5,985,890 A | 11/1999 | Cottens et al. |
| 6,011,018 A | 1/2000 | Crabtree et al. |
| 6,025,137 A | 2/2000 | Shyjan |
| 6,028,174 A | 2/2000 | Ullrich et al. |
| 6,034,218 A | 3/2000 | Reed et al. |
| 6,051,230 A | 4/2000 | Thorpe et al. |
| 6,054,265 A | 4/2000 | Barney et al. |
| 6,166,011 A | 12/2000 | Wythes et al. |
| 6,200,985 B1 | 3/2001 | Cottens et al. |
| 6,251,932 B1 | 6/2001 | Reichelt et al. |
| 6,252,058 B1 | 6/2001 | Thompson |
| 6,261,535 B1 | 7/2001 | Thorpe et al. |
| 6,261,766 B1 | 7/2001 | Diamandis |
| 6,313,264 B1 | 11/2001 | Caggiano et al. |
| 6,319,891 B1 | 11/2001 | Sontheimer et al. |

OTHER PUBLICATIONS

Nair et al., "Molecular Cloning of Human FKBP51 and Comparisons of Immunophilin Interactions with Hsp90 and Progesterone Receptor," *Molecular and Cellular Biology*, vol. 17, No. 2, Feb. 1997, pp 594–595.

Cleutjens, et al., "Two Androgen Response Regions Cooperate in Steroid Hormone Regulated Activity of the Prostate–specific Antigen Promoter," *The Journal of Biological Chemistry*, vol. 271, No. 11, Mar. 15, 1996, pp 6379–6388.

Henttu, et al., "Androgens Up–Regulate the Human Prostate–Specific Antigen Messenger Ribonucleic Acid (mRNA), but Down–Regulate the Prostatic Acid Phosphatase mRNA in the LNCaP Cell Line," *Endocrinology*, vol. 130, No. 2, 1992, pp 772.

Horoszewicz, et al., "LNCaP Model of Human Prostatic Carcinoma[1]," *Cancer Research*, vol. 43, Apr. 1983, pp 1809–1818.

Kokontis, et al., "Increased Androgen Receptor Activity and Altered c–myc Expression in Prostate Cancer Cells after Long–Term Androgen Deprivation[1]," *Cancer Research*, vol. 54, Mar. 15, 1992, pp 1566–1573.

Murtha, et al., "Androgen Induction of a Human Prostate–Specific Kallikrein, hKLK2: Characterization of an Androgen Response Element in the 5' Promoter Region of the Gene†," *Biochemistry*, vol. 32, 1993, pp 6459–6464.

Schuumans, et al., "Regulation Of Growth Of LNCaP Human Prostate Tumor Cells By Growth Factors And Steroid Hormones," *J. Steroid Biochem. Molec. Biol.*, vol. 40, No. 1–3, 1991, pp 193–197.

Silverstein et al., "Different Regions of the Immunophilin FKBP52 Determine Its Association With the Glucocorticoid Receptor, hsp90, and Cytoplasmic Dynein," *Journal of Biological Chemistry*, vol. 274, No. 52, D c. 24, 1999, pp 36980–36986.

Smith et al., "FKPB54, a Novel FK506–Binding Protein in Avian Progesterone Receptor Complexes and HeLa Extracts," *Journal of Biological Chemistry*, vol. 268, No. 32, Nov. 15, 1993, pp 24270–24273.

Swinnen, et al., "Androgen regulation of the messenger RNA encoding diazepam–binding inhibitor/acyl–CoA–binding protein in the human prostatic adenocarcinoma cell line LNCaP," *Molecular and Cellular Endocrinology*, vol. 104, 1994, pp 153–162.

Swinnen, et al.,"Androgens Markedly Stimulate the Accumulation of Neutral Lipids in the Human Prostatic Adenocarcinoma Cell Line LNCaP," *Endocrinoloy*, vol. 137, No. 10, 1996, pp 4468–4474.

Tamayo, et al., "Interpreting patterns of gene expression with self–organizing maps: Methods and application to hematopoietic differentiation," *Proc. Natl. Acad. Sci. USA*, vol. 96, Mar. 1999, pp 2907–2912.

Ulrix et al., "Androgens Down–Regulate the Expression of the Human Homologue of Paternally Expressed Gene–3 in the Prostatic Adenocarcinoma Cell Line LNCaP," *Molecular and Cellular Endocrinology*, vol. 155, 1999, pp 69–76.

Ward et al., "Expression of the Estrogen Receptor–Associate Immunophilins, Cyclophilin 40 and FKPB52, in Breast Cancer," *Breast Cancer Research and Treatment*, vol. 58, 1999, pp 267–280.

Yang et al., "Differential Expression and Androgen Regulation of the Human Selenium–Binding Protein Gene hSP56 in Prostate Cancer Cells," *Cancer Research*, vol. 58, Jul. 15, 1998, pp 3150–3153.

SEQUENCE LISTING

<160> NUMBER OF SEQ ID NOS: 6

<210> SEQ ID NO 1
<211> LENGTH: 16
<212> TYPE: DNA
<213> ORGANISM: Homo sapiens

<400> SEQUENCE: 1
cgtggccaac ccctga                                                    16

<210> SEQ ID NO 2
<211> LENGTH: 20
<212> TYPE: DNA
<213> ORGANISM: Homo sapiens

<400> SEQUENCE: 2
cttggcctgg tcatttccaa                                                20

<210> SEQ ID NO 3
<211> LENGTH: 35
<212> TYPE: DNA
<213> ORGANISM: Homo sapiens

<400> SEQUENCE: 3
cacccctatc aaccccctat tgtagtaaac ttgga                               35

<210> SEQ ID NO 4
<211> LENGTH: 19
<212> TYPE: DNA
<213> ORGANISM: Homo sapiens

<400> SEQUENCE: 4
ctgtgacaag gcccttgga                                                 19

<210> SEQ ID NO 5
<211> LENGTH: 19
<212> TYPE: DNA
<213> ORGANISM: Homo sapiens

```
<400> SEQUENCE: 5
ctgggcttca cccctccta                                                    19

<210> SEQ ID NO 6
<211> LENGTH: 27
<212> TYPE: DNA
<213> ORGANISM: Homo sapiens

<400> SEQUENCE: 6
acaagccttt ctcattggca ctgtcca                                           27
```

EXPRESSION ANALYSIS OF FKBP NUCLEIC ACIDS AND POLYPEPTIDES USEFUL IN THE DIAGNOSIS OF PROSTATE CANCER

RELATED APPLICATION

This application claims the benefit of U.S. Provisional Patent Application Ser. No. 60/253,539, filed Nov. 28, 2000, entitled "Expression Analysis of FKBP54 Nucleic Acids and Polypeptides Useful in the Diagnosis and Treatment of Prostate Cancer". The teachings of the foregoing application is incorporated herein by reference.

BACKGROUND OF THE INVENTION

Prostate cancer is the second most common cause of cancer related death and will kill an estimated 37,000 people this year alone. The prostate gland, which is found exclusively in male mammals, produces several regulatory peptides. The prostate gland comprises stroma and epithelium cells, the latter group consisting of columnar secretory cells and basal non-secretory cells. A proliferation of these basal cells, as well as stroma cells gives rise to benign prostatic hyperplasia (BPH) which is one common prostate disease. Another common prostate disease is prostatic adenocarcinoma (CaP), the most common of the fatal pathophysiological prostate cancers. Prostatic adenocarcinoma involves a malignant transformation of epithelial cells in the peripheral region of the prostate gland. Prostatic adenocarcinoma and benign prostatic hyperplasia are two common prostate diseases which have a high rate of incidence in the aging human male population. Approximately one out of every four males above the age of 55 suffers from a prostate disease of some form or another.

To date, various substances that are synthesized and secreted by normal, benign and cancerous prostates are used as tumor markers to gain an understanding of the pathogenesis of the various prostate diseases and in the diagnosis of prostate disease. The three predominant proteins or peptides secreted by a normal prostate gland are Prostatic Acid Phosphatase (PAP), Prostate Specific Antigen (PSA) and prostatic inhibin (PIP) also known as human seminal plasma inhibin (HSPI). Both PSA and PAP have been studied as tumour markers in the detection of prostate disease but since both exhibit elevated levels in prostates having benign prostatic hyperplasia (BPM) neither marker is specific and therefore are of limited use.

Despite the available knowledge, little is known about the genetic basis underlying the prostate cancer disease and the androgen-regulated genes that may be involved with its progression. Although androgens have been known to play a major role in the biology of prostate cancer. However, the full complexity of the hormonal regulation has not been completely covered and more androgen related processes are being elucidated. Many of these processes involve several molecules associated in prostate cancer that remain elusive. In addition, there may be several known molecules that have not yet been associated with the pathogenesis of the disease. Accordingly, a need exists for identifying unknown molecules that may be involved in prostate cancer and the genes encoding them. A need also exists for identifying known molecules that have not yet been implicated in the pathogenesis of prostate cancer, particularly those that can serve as targets for the diagnosis, prevention, and treatment of prostate cancer.

SUMMARY OF THE INVENTION

The invention is based, in part, on the discovery of a number of genes which are androgen-inducible in androgen-dependent prostate cancer cells (e.g., LNCaP cells). These genes serve as markers suitable for detection, diagnosis and prognosis of prostate disorders. This invention provides methods and screening assays for the detection and diagnosis of prostate cancer. The primary screening assays detect an alteration in the expression level of genes associated with prostate cancer. In particular, this invention provides for the use of immunophilins, such as FK-Binding Proteins (FKBPs), e.g., FKBP54, as genetic markers for the detection, diagnosis and prognosis of prostate disorders. Immunophilins are proteins that serve as receptors for the immunosuppressant drugs such as cyclosporin A (CsA), FK506, and rapamycin. Known classes of immunophilins include cyclophilins, and FKS506 binding proteins, such as FKBPs. Cyclosporin A binds to cyclophilin while FK506 and rapamycin bind to FKBP. These immunophilin-drug complexes interface with a variety of intracellular signal transduction systems. Immunophilins are known to have peptidyl-prolyl isomerase (PPIase) or rotamase enzyme activity. It has been determined that rotamase activity has a role in the catalyzation of the interconversion of the cis and trans isomer of immunophilin proteins.

FKBP54 is a member of the immunophilin family and has been associated with the progesterone receptor complex as described by Smith et al. (1993) *J. Biol. Chem.* 268: 18365–18371. The invention provides for use of immunophilins, e.g., FKBP54, that are up-regulated (increased mRNA and protein expression/activated/agonized) or down-regulated (decreased mRNA and protein expression/suppressed/antagonized) in the presence of androgens.

Using gene cluster analysis, the expression pattern of FKBP54 was found to be similar to that of prostate specific antigen (PSA), which has been used to diagnose prostate cancer patient. The present study described herein demonstrates the up-regulation of FKBP54 in the presence of androgen and can be used as a marker for the detection, diagnosis and prognosis of prostate disorders. In addition, quantitative PCR was used to confirm gene expression of the target marker. The transcription level of FKBP54 was found to be regulated by androgen, demonstrating a time dependent increase in transcription. Western blot analysis of the expressed FKBP54 protein further confirmed the time dependent increase in expression levels in the presence of androgen. The presence of FKBP54 in solid tumors was also demonstrated. Furthermore, transient cotransfection studies in COS cells showed that androgen receptor activation was enhanced by FKBP54.

In one embodiment, the invention provides a method of assessing whether a subject is afflicted with prostate cancer, by comparing the level of expression of the FK-binding proteins, e.g., FKBP54 marker in a sample from a subject, to the normal level of expression of the marker in a control sample, where a significant difference between the level of expression of the marker in the sample from the subject and the normal level is an indication that the subject is afflicted with prostate cancer. In a preferred embodiment, the marker corresponds to a transcribed polynucleotide or portion thereof, where the polynucleotide includes the marker. In a particularly preferred embodiment, the level of expression of the marker in the sample differs from the normal level of expression of the marker in a subject not afflicted with prostate cancer by a factor of at least two, and in an even more preferred embodiment, the expression levels differ by a factor of at least three. In another preferred embodiment, the marker is not significantly expressed in non-prostate cancer cells.

In another preferred embodiment, the sample includes cells obtained from the subject. In another preferred embodiment, the level of expression of the marker in the sample is assessed by detecting the presence in the sample of a protein corresponding to the marker. In a particularly preferred embodiment, the presence of the protein is detected using a reagent which specifically binds with the protein. In an even more preferred embodiment, the reagent is selected from the group of reagents including an antibody, an antibody derivative, and an antibody fragment. In another preferred embodiment, the level of expression of the marker in the sample is assessed by detecting the presence in the sample of a transcribed polynucleotide or portion thereof, where the transcribed polynucleotide includes the marker. In a particularly preferred embodiment, the transcribed polynucleotide is an mRNA or a cDNA. In another particularly preferred embodiment, the step of detecting further comprises amplifying the transcribed polynucleotide.

In yet another preferred embodiment, the level of expression of the FKBP marker, e.g., FKBP54 marker in the sample is assessed by detecting the presence in the sample of a transcribed polynucleotide which anneals with the marker or anneals with a portion of a polynucleotide under stringent hybridization conditions, where the polynucleotide includes the marker. The level of expression of the marker is significantly altered, relative to the corresponding normal levels of expression the marker, is an indication that the subject is afflicted with prostate cancer.

In another embodiment, the invention provides a method for monitoring the progression of prostate cancer in a subject, including detecting in a subject sample at a first point in time the expression of the FKBP marker, e.g., FKBP54 marker, repeating this detection step at a subsequent point in time, and comparing the level of expression detected in the two detection steps, and monitoring the progression of prostate cancer in the subject using this information. In another preferred embodiment, the marker corresponds to a transcribed polynucleotide or portion thereof, where the polynucleotide includes the marker. In another preferred embodiment, the sample includes cells obtained from the subject. In a particularly preferred embodiment, the cells are collected from skin or blood tissue.

In another embodiment, the invention provides a method of assessing the efficacy of a test compound for inhibiting prostate cancer in a subject, including comparing expression of the FKBP54 marker in a first sample obtained from the subject which is exposed to or maintained in the presence of the test compound, to expression of the FKBP marker, e.g., FKBP54 marker in a second sample obtained from the subject, where the second sample is not exposed to the test compound, where a significantly lower level of expression of the marker in the first sample relative to that in the second sample is an indication that the test compound is efficacious for inhibiting prostate cancer in the subject. In a preferred embodiment, the first and second samples are portions of a single sample obtained from the subject. In another preferred embodiment, the first and second samples are portions of pooled samples obtained from the subject.

In another embodiment, the invention provides a method of assessing the efficacy of a therapy for inhibiting prostate cancer in a subject, the method including comparing expression of the FKBP marker, e.g., FKBP54 marker in the first sample obtained from the subject prior to providing at least a portion of the therapy to the subject, to expression of the marker in a second sample obtained form the subject following provision of the portion of the therapy, where a significantly lower level of expression of the marker in the second sample relative to the first sample is an indication that the therapy is efficacious for inhibiting prostate cancer in the subject.

In another embodiment, the invention provides a method of selecting a composition for inhibiting prostate cancer in a subject, the method including obtaining a sample including cells from a subject, separately maintaining aliquots of the sample in the presence of a plurality of test compositions, comparing expression of the FKBP marker, e.g., FKBP54 marker in each of the aliquots, and selecting one of the test compositions which induces a lower level of expression of the FKBP marker, e.g., FKBP54 marker in the aliquot containing that test composition, relative to other test compositions.

In another embodiment, the invention provides a method of inhibiting prostate cancer in a subject, including obtaining a sample including cells from a subject, separately maintaining aliquots of the sample in the presence of a plurality of test compositions, comparing expression of the FKBP marker, e.g., FKBP54 marker in each of the aliquots, and administering to the subject at least one of the test compositions which induces a lower level of expression of the FKBP marker, e.g., FKBP54 marker in the aliquot containing that test composition, relative to other test compositions.

In another embodiment, the invention provides a method of assessing the potential of a test compound to trigger prostate cancer in a cell, including maintaining separate aliquots of cells in the presence and absence of the test compound, and comparing expression of the FKBP marker, e.g., FKBP54 marker in each of the aliquots, where a significantly enhanced level of expression of the FKBP marker, e.g., FKBP54 marker in the aliquot maintained in the presence of the test compound, relative to the aliquot maintained in the absence of the test compound, is an indication that the test compound possesses the potential for triggering prostate cancer in a cell.

In another embodiment, the invention provides a method of treating a subject afflicted with prostate cancer, including providing to cells of the subject afflicted with prostate cancer a protein corresponding to the FKBP marker, e.g., FKBP54 marker. In a preferred embodiment, the protein is provided to the cells by providing a vector including a polynucleotide encoding the FKBP protein, e.g., FKBP54 protein to the cells.

In another embodiment, the invention provides a method of treating a subject afflicted with prostate cancer an antisense oligonucleotide complementary to a polynucleotide corresponding to the FKBP marker, e.g., FKBP54 marker.

In another embodiment, the invention provides a method of inhibiting prostate cancer in a subject at risk for developing prostate cancer, including inhibiting expression of a gene corresponding to the FKBP marker, e.g., FKBP54 marker.

Other features and advantages of the invention will be apparent from the following detailed description and claims.

DETAILED DESCRIPTION OF THE INVENTION

Figure 1:
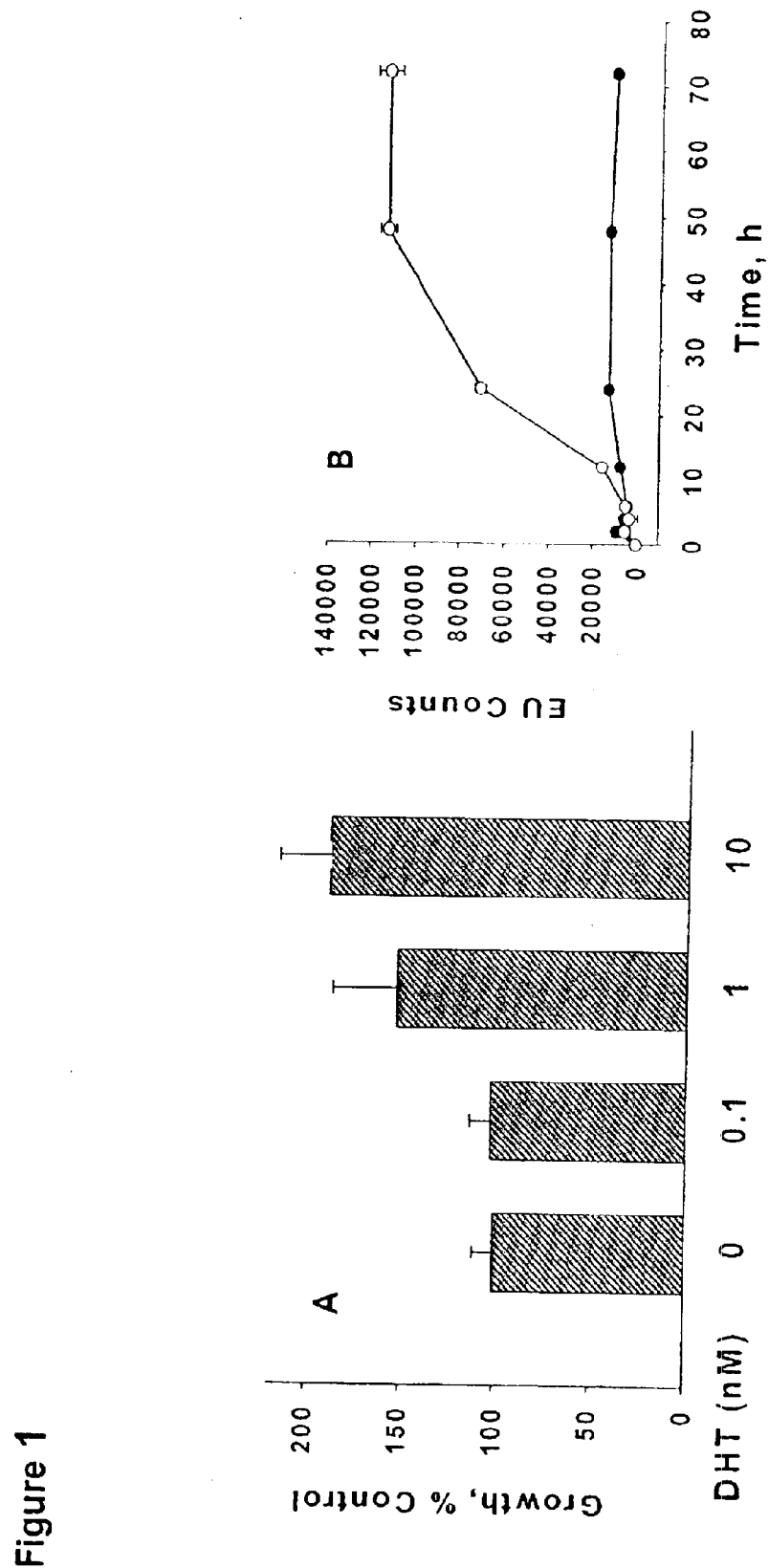
FIG. 1A is a bar chart depicting the effect of dihydrotestosterone (DHT) on the growth and PSA production of LNCaP cells plated at 20,000 cells/well in a 24-well plate with 1 ml of medium. Cells were treated with DHT as shown, and cell growth was determined by 3-(4,5-dimethylthiazol-2-yl)-2,5-diphenyltetrazolium bromide (MTT) assay on day 3.
FIG. 1B is a graph depicting the effect of DHT on the growth and PSA production of LNCaP cells plated at $1 \times 10^6$ cells/well in a 175 cm² flask. Cells were treated with or without 10 nM DHT the next day, and were harvested for RNA preparation and PSA analysis.

The invention relates, in part, to newly discovered correlation between the expression of selected markers and the presence of prostate cancer in a subject, in particular, immunophilins such as the FK binding proteins (FKBPs), e.g., FKBP54. The term "FKBP54" is used herein synonymously with the term "FKBP51". FKBP54 is a member of the immunophilin family. Other FK binding proteins include, but are not limited to, FKBP12 (Hidalgo et al. (2000) *Oncogene* 19:6680–6686, Genbank Accession No. AF 3222070), FKBP12.6 (Deivanayagam et al. (2000) *Acta. Crystallogr. D. Biol. Crystallog* 56: 266–271, Accession No. L37086), and FKBP52 (Yamamoto-Yamaguchi et al. (2001) *Exp Hematol* 29:582–588, Genbank Accession No. M88279).

The relative levels of expression of the FK binding protein marker, e.g., FKBP54 marker, has been found to be indicative of a predisposition in the subject to prostate cancer and/or diagnostic of the presence or potential presence of prostate cancer in a subject. The invention features the FKBP marker, e.g., FKBP54, methods for detecting the presence or absence of prostate cancer in a sample or subject, and methods of predicting the incidence of prostate cancer in a sample or subject using the FKBP marker, e.g., FKBP54. The invention also provides methods by which prostate cancer may be treated using the FKBP marker, e.g., FKBP54.

The present invention is based, at least in part, on the identification of the genetic marker, FKBP54, which is differentially expressed in samples from androgen dependent prostate cancer cells. A panel of 6800 known genes was screened for expression androgen dependent prostate cancer cells (see Example 1). Those genes with statistically significant (p<0.05) differences between the diseased and normal tissues were identified. This differential expression was observed either as a decrease in expression, or an increase in expression. The expression of these selected genes in androgen dependent prostate cancer cells was assessed by GENE-CHIP® analysis, as described in Example 1. FKBP54 was found to increase in expression in LNCaP prostate cancer cells. The growth of LNCaP cells and the production of PSA were responsive to a natural androgen receptor (AR) ligand, DHT, LNCaP and are suitable model for gene expression profiling. (See e.g., Kokontis et al. (1994) *Cancer Res.* 54: 1566–1573; Schuurmans et al. (1991) *J. Steroid Biochem. Mol. Biol.* 40:193–197; Swinnen et al. (1994) *Molec. Cell. Endocrinol.* 104: 153–162; Cleutjens et al.(1996) *J. Biol. Chem.* 271: 6379–6388; Henttu et al. (1992) *Endocrinology* 130: 766–772; Murtha et al. (1993) *Biochem.* 32: 6459–6464; Swinnen et al. (1996) Endocrinol. 137: 4468–4474).

As an internal control, the prostate specific antigen (PSA) gene, known in the art to be implicated in prostate cancer, was included to screen androgen dependent prostate cancer cells. PSA was found to be significantly increased in expression in androgen dependent prostate cancer cells.

Accordingly, the present invention pertains to the use of the FKBP genes (e.g., the DNA or cDNA of FKBP54), the corresponding mRNA transcripts, and the encoded polypeptides, as a marker for the presence or risk of development prostate cancer. The FKBP marker, e.g., FKBP54 is useful to correlate the extent and/or severity of disease. The FKBP marker, e.g., FKBP54 marker can be useful in the treatment of prostate cancer, or in assessing the efficacy of a treatment for cancer. In addition, the FKBP marker, e.g., FKBP54 marker can also be used in screening assays to identify compound or agents that modify the expression of the marker and the disease state.

In one aspect, the invention provides the FKBP marker, e.g., FKBP54 marker whose quantity or activity is correlated with the presence of prostate cancer. The FKBP marker, e.g., FKBP54 marker of the invention may be nucleic acid molecules (e.g., DNA, cDNA, or RNA) or polypeptides. The FKBP marker, e.g., FKBP54 marker can be either increased or decreased in quantity or activity in prostate cancer tissue as compared to non-prostate cancer tissue. For example, the gene designated "FKBP54" (accession number U42031) is increased in expression level in androgen dependent prostate cancer cell samples. Both the presence of increased or decreased mRNA for this gene, and also increased or decreased levels of the protein products of this gene serve as markers of prostate cancer. Preferably, increased and decreased levels of the FKBP marker, e.g., FKBP54 marker of the invention are increases and decreases of a magnitude that is statistically significant as compared to appropriate control samples (e.g., samples not affected with prostate cancer). In particularly preferred embodiments, the FKBP marker, e.g., FKBP54 marker is increased or decreased relative to control samples by at least 2-, 3-, 4-, 5-, 6-, 7-, 8-, 9-, or 10-fold or more. Similarly, one skilled in the art will be cognizant of the fact that a preferred detection methodology is one in which the resulting detection values are above the minimum detection limit of the methodology.

Measurement of the relative amount of an RNA or protein marker of the invention may be by any method known in the art (see, e.g., Sambrook, J., Fritsh, E. F., and Maniatis, T. *Molecular Cloning: A Laboratory Manual 2nd, ed., Cold Spring Harbor Laboratory*, Cold Spring Harbor Laboratory Press, Cold Spring Harbor, N.Y., 1989; and *Current Protocols in Molecular Biology*, eds. Ausubel et al. John Wiley & Sons: 1992). Typical methodologies for RNA detection include RNA extraction from a cell or tissue sample, followed by hybridization of a labeled probe (e.g., a complementary nucleic acid molecule) specific for the target RNA to the extracted RNA, and detection of the probe (e.g. Northern blotting). Typical methodologies for protein detection include protein extraction from a cell or tissue sample, followed by hybridization of a labeled probe (e.g., an antibody) specific for the target protein to the protein sample, and detection of the probe. The label group can be a radioisotope, a fluorescent compound, an enzyme, or an enzyme co-factor. Detection of specific protein and nucleic acid molecules may also be assessed by gel electrophoresis, column chromatography, direct sequencing, or quantitative PCR (in the case of nucleic acid molecules) among many other techniques well known to those skilled in the art.

In certain embodiments, the FKBP gene itself (e.g., the FKBP54 DNA or cDNA), may serve as a marker for prostate cancer. For example, the absence of nucleic acids corresponding to the FKBP54 gene, such as by deletion of all or part of the gene, may be correlated with disease. Similarly, an increase of nucleic acid corresponding to the FKBP54 gene, such as by duplication of the gene, may also be correlated with disease.

Detection of the presence or number of copies of all or a part of a FKBP gene, e.g., FKBP54 gene of the invention may be performed using any method known in the art. Typically, it is convenient to assess the presence and/or quantity of a DNA or cDNA by Southern analysis, in which total DNA from a cell or tissue sample is extracted, is hybridized with a labeled probe (e.g., a complementary DNA molecule), and the probe is detected. The label group can be a radioisotope, a fluorescent compound, an enzyme, or an enzyme co-factor. Other useful methods of DNA detection and/or quantification include direct sequencing, gel electrophoresis, column chromatography, and quantitative PCR, as is known by one skilled in the art.

The invention also encompasses nucleic acid and protein molecules which are structurally different from the molecules described above (e.g., which have a slightly altered nucleic acid or amino acid sequence), but which have the same properties as the molecules above (e.g., encoded amino acid sequence, or which are changed only in nonessential amino acid residues). Such molecules include allelic variants, and are described in greater detail in subsection I.

In another aspect, the invention provides the FKBP marker, e.g., FKBP54 marker whose quantity or activity is correlated with the severity of prostate cancer. This FKBP marker, e.g., FKBP54 marker is either increased or decreased in quantity or activity in prostate cancer tissue in a fashion that is either positively or negatively correlated with the degree of severity of prostate cancer. In yet another aspect, the invention provides the FKBP marker, e.g., FKBP54 marker whose quantity or activity is correlated with a risk in a subject for developing prostate cancer. The FKBP marker, e.g., FKBP54 marker is either increased or decreased in activity or quantity in direct correlation to the likelihood of the development of prostate cancer in a subject.

It will also be appreciated by one skilled in the art that the FKBP marker, e.g., FKBP54 of the invention may conveniently be provided on solid supports. For example, polynucleotides, such as mRNA, may be coupled to an array (e.g., a GENECHIP®, array for hybridization analysis), to a resin (e.g., a resin which can be packed into a column for column chromatography), or a matrix (e.g., a nitrocellulose matrix for northern blot analysis). The immobilization of molecules complementary to the marker(s), either covalently or noncovalently, permits a discrete analysis of the presence or activity of each marker in a sample. In an array, for example, polynucleotides complementary to the full length or a portion of the FKBP marker, e.g., FKBP54 marker may individually be attached to different, known locations on the array. The array may be hybridized with, for example, polynucleotides extracted from a skin cell sample from a subject. The hybridization of polynucleotides from the sample with the array at any location on the array can be detected, and thus the presence or quantity of the marker in the sample can be ascertained. In a preferred embodiment, a GENECHIP®, array is employed (Affymetrix). Similarly, Western analyses may be performed on immobilized antibodies specific for the FKBP polypeptide (e.g., FKBP54) marker hybridized to a protein sample from a subject. In addition, quantitative PCR was used to confirm gene expression of the target marker. The transcription level of FKBP54 was found to be regulated by androgen, demonstrating a time dependent increase in transcription. Western blot analysis of the expressed FKBP54 protein further confirmed the time dependent increase in expression levels in the presence of androgen. The presence of FKBP54 in solid tumors was also demonstrated. Furthermore, transient cotransfection studies in COS cells showed that androgen receptor activation was enhanced by FKBP54.

It will also be apparent to one skilled in the art that the entire FKBP marker, e.g., FKBP54 marker protein or nucleic acid molecule need not be conjugated to the support; a portion of the marker of sufficient length for detection purposes (e.g., for hybridization), for example, a portion of the marker which is 7, 10, 15, 20, 25, 30, 35, 40, 45, 50, 55, 60, 65, 70, 75, 100 or more nucleotides or amino acids in length may be sufficient for detection purposes.

The FKBP, e.g., FKBP54 nucleic acid and protein marker of the invention may be isolated from any tissue or cell of a subject. In a preferred embodiment, the tissue is prostate cells or tissue. However, it will be apparent to one skilled in the art that other tissue samples, including bodily fluids (e.g., urine, bile, serum, lymph, saliva, mucus and pus) and other tissue samples may also serve as sources from which the markers of the invention may be isolated, or in which the presence, activity, and/or quantity of the markers of the invention may be assessed. The tissue samples containing one or more of the markers themselves may be useful in the methods of the invention, and one skilled in the art will be cognizant of the methods by which such samples may be conveniently obtained, stored, and/or preserved.

Several markers were known prior to the invention to be associated with prostate cancer, e.g., PSA. These markers are not included with the marker of the invention. However, these markers may be conveniently be used in combination with the marker of the invention in the methods, panels, and kits of the invention.

In another aspect, the invention provides methods of making an isolated hybridoma which produces an antibody useful for assessing whether a patient is afflicted with prostate cancer. In this method, a protein corresponding to the FKBP marker, e.g., FKBP54 marker is isolated (e.g., by purification from a cell in which it is expressed or by transcription and translation of a nucleic acid encoding the protein in vivo or in vitro using known methods. A vertebrate, preferably a mammal such as a mouse, rat, rabbit, or sheep, is immunized using the isolated protein or protein fragment. The vertebrate may optionally (and preferably) be immunized at least one additional time with the isolated protein or protein fragment, so that the vertebrate exhibits a robust immune response to the protein or protein fragment. Splenocytes are isolated from the immunized vertebrate and fused with an immortalized cell line to form hybridomas, using any of a variety of methods well known in the art. Hybridomas formed in this manner are then screened using standard methods to identify one or more hybridomas which produce an antibody which specifically binds with the protein or protein fragment. The invention also includes hybridomas made by this method and antibodies made using such hybridomas.

The invention provides methods of identifying prostate cancer, or risk of developing prostate cancer in a subject. These methods involve isolating a sample from a subject (e.g., a sample containing prostate cancer cells or blood cells), detecting the presence, quantity, and/or activity of the FKBP marker, e.g., FKBP54 marker of the invention in the sample relative to a second sample from a subject known not to have prostate cancer. The levels of the FKBP marker, e.g., FKBP54 marker in the two samples are compared, and a significant increase in the marker in the test sample indicates the presence or risk of presence of prostate cancer in the subject.

The invention also provides methods of assessing the severity of prostate cancer in a subject. These methods involve isolating a sample from a subject (e.g., a sample containing prostate cancer cells or blood cells), detecting the presence, quantity, and/or activity of the FKBP marker, e.g., FKBP54 marker of the invention in the sample relative to a second sample from a subject known not to have prostate cancer. The level of the FKBP marker, e.g., FKBP54 marker in the two samples are compared, and a significant increase in the marker in the test sample is correlated with the degree of severity of prostate cancer in the subject.

The invention also provides methods of treating (e.g., inhibiting prostate cancer in a subject. These methods involve isolating a sample from a subject (e.g., a sample containing prostate cancer cells or blood cells), detecting the presence, quantity, and/or activity of FKBP marker, e.g., FKBP54 in the sample relative to a second sample from a subject known not to have prostate cancer. The levels of the FKBP marker, e.g., FKBP54 marker in the two samples are compared, and significant increases or decreases in one or more markers in the test sample relative to the control sample are observed. For markers that are significantly decreased in expression or activity, the subject may be administered that expressed marker protein, or may be treated by the introduction of MRNA or DNA corresponding to the decreased marker (e.g., by gene therapy), to thereby increase the levels of the marker protein in the subject. For markers that are significantly increased in expression or activity, the subject may be administered mRNA or DNA antisense to the increased marker (e.g. by gene therapy), or may be administered antibodies specific for the marker protein, to thereby decrease the levels of the marker protein in the subject. In this manner, the subject may be treated for prostate cancer.

The invention also provides methods of preventing the development prostate cancer in a subject. These methods involve, for markers that are significantly decreased in expression or activity, the administration of that marker protein, or the introduction of mRNA or DNA corresponding to the decreased marker (e.g., by gene therapy), to thereby increase the levels of the marker protein in the subject. For markers that are significantly increased in expression or activity, the subject may be administered mRNA or DNA antisense to the increased marker (e.g., by gene therapy), or may be administered antibodies specific for the marker protein, to thereby decrease the levels of the marker protein in the subject. In this manner, the development prostate cancer in a subject may be prevented.

The invention also provides methods of assessing a treatment or therapy for prostate cancer condition in a subject. These methods involve isolating a sample from a subject (e.g., a sample containing prostate cancer cells or blood cells) suffering from prostate cancer who is undergoing a treatment or therapy, detecting the presence, quantity, and/or activity of the FKBP marker, e.g., FKBP54 marker of the invention in the first sample relative to a second sample from a subject afflicted prostate cancer who is not undergoing any treatment or therapy for the condition, and also relative to a third sample from a subject unafflicted by prostate cancer. The levels of FKBP marker, e.g., FKBP54 marker in the three samples are compared, and significant increases or decreases the FKBP marker, e.g., FKBP54 marker in the first sample relative to the other samples are observed, and correlated with the presence, risk of presence, or severity prostate cancer. By assessing prostate cancer has been lessened or alleviated in the sample, the ability of the treatment or therapy to treat prostate cancer is also determined.

The invention also provides methods for diagnosing androgen-dependent prostate cancer in a subject. The method involves isolating a sample from a subject (e.g., a sample containing prostate cancer cells or blood cells) who is suffering from prostate cancer, measuring the level of expression of the FKBP marker, e.g., FKBP54 marker in the presence and absence of androgen and comparing the difference in expression of the FKBP marker, e.g., FKBP54 marker in the presence and absence of androgen. The prostate cancer cells are androgen dependent if the expression of the marker is increased in the presence of androgen compared to the absence of androgen.

The invention also provides methods for determining the efficacy of androgen withdrawal treatment in a subject afflicted with prostate cancer. The method involves detecting in a subject sample at a first point in time, the expression level of the FKBP marker,
  e.g., FKBP54 marker; and detecting the expression level of the FKBP marker, e.g., FKBP54 marker at a subsequent point in time occurring after the subject begins androgen withdrawal treatment. The level of expression of the FKBP marker, e.g., FKBP54 marker detected at the first and second time points is compared. A decrease in the level of expression indicates that the androgen withdrawal treatment has decreased efficacy.

The invention also provides pharmaceutical compositions for the treatment of prostate cancer. These compositions may include a marker protein and/or nucleic acid of the invention (e.g., for those markers which are decreased in quantity or activity in prostate cancer cell sample versus non-prostate cancer cell sample), and can be formulated as described herein. Alternately, these compositions may include an antibody which specifically binds to a marker protein of the invention and/or an antisense nucleic acid molecule which is complementary to a marker nucleic acid of the invention (e.g., for those markers which are increased in quantity or activity in a prostate cancer cell sample versus non-prostate cancer cell sample), and can be formulated as described herein.

The invention also provides kits for assessing the presence of prostate cancer in a sample (e.g., a sample from a subject at risk for prostate cancer), the kit comprising an antibody, wherein the antibody specifically binds with a protein corresponding to the FKBP marker, e.g., FKBP54 marker.

The invention further provides kits for assessing the presence of prostate cancer in a sample from a subject (e.g., a subject at risk for prostate cancer), the kit comprising a nucleic acid probe wherein the probe specifically binds with a transcribed polynucleotide corresponding to the FKBP marker, e.g., FKBP54 marker.

The invention further provides kits for assessing the suitability of each of a plurality of compounds for inhibiting prostate cancer in a subject. Such kits include a plurality of compounds to be tested, and a reagent for assessing expression of the FKBP marker, e.g., FKBP54 marker.

Modifications to the above-described compositions and methods of the invention, according to standard techniques, will be readily apparent to one skilled in the art and are meant to be encompassed by the invention.

To facilitate an understanding of the present invention, a number of terms and phrases are defined below:

As used herein, the terms "polynucleotide" and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for guanine when the polynucleotide is RNA. This, the term "polynucleotide sequence" is the alphabetical representation of a polynucleotide molecule. This alphabetical representation can be inputted into databases in a computer having a central processing unit and used for bioinformatics applications such as functional genomics and homology searching.

A "gene" includes a polynucleotide containing at least one open reading frame that is capable of encoding a particular polypeptide or protein after being transcribed and translated. Any of the polynucleotide sequences described herein may be used to identify larger fragments or full-length coding sequences of the gene with which they are associated. Methods of isolating larger fragment sequences are known to those of skill in the art, some of which are described herein.

A "gene product" includes an amino acid (e.g., peptide or polypeptide) generated when a gene is transcribed and translated.

A "probe" when used in the context of polynucleotide manipulation includes an oligonucleotide that is provided as a reagent to detect a target present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and proteins, including enzymes.

A "primer" includes a short polynucleotide, generally with a free 3'-OH group that binds to a target or "template" present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are well known in the art, and are taught, for example, in MacPherson et al., IRL Press at Oxford University Press (1991)). All processes of producing replicate copies of a polynucleotide, such as PCR or gene cloning, are collectively referred to herein as "replication". A primer can also be used as a probe in hybridization reactions, such as Southern or Northern blot analyses (see, e.g., Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

The term "cDNAs" includes complementary DNA, that is mRNA molecules present in a cell or organism made into cDNA with an enzyme such as reverse transcriptase. A "cDNA library" includes a collection of mRNA molecules present in a cell or organism, converted into cDNA molecules with the enzyme reverse transcriptase, then inserted into "vectors" (other DNA molecules that can continue to replicate after addition of foreign DNA). Exemplary vectors for libraries include bacteriophage, viruses that infect bacteria (e.g., lambda phage). The library can then be probed for the specific cDNA (and thus mRNA) of interest.

A "gene delivery vehicle" includes a molecule that is capable of inserting one or more polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, viruses and viral vectors, such as baculovirus, adenovirus, and retrovirus, bacteriophage, cosmid, plasmid, fungal vector and other recombination vehicles typically used in the art which have been described for replication and/or expression in a variety of eukaryotic and prokaryotic hosts. The gene delivery vehicles may be used for replication of the inserted polynucleotide, gene therapy as well as for simply polypeptide and protein expression.

A "vector" includes a self-replicating nucleic acid molecule that transfers an inserted polynucleotide into and/or between host cells. The term is intended to include vectors that function primarily for insertion of a nucleic acid molecule into a cell, replication vectors that function primarily for the replication of nucleic acid and expression vectors that function for transcription and/or translation of the DNA or RNA. Also intended are vectors that provide more than one of the above function.

A "host cell" is intended to include any individual cell or cell culture which can be or has been a recipient for vectors or for the incorporation of exogenous nucleic acid molecules, polynucleotides and/or proteins. It also is intended to include progeny of a single cell. The progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, insect cells, animal cells, and mammalian cells, e.g., murine, rat, simian or human cells.

The term "genetically modified" includes a cell containing and/or expressing a foreign gene or nucleic acid sequence which in turn modifies the genotype or phenotype of the cell or its progeny. This term includes any addition, deletion, or disruption to a cell's endogenous nucleotides.

As used herein, "expression" includes the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989). Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general.

"Differentially expressed", as applied to a gene, includes the differential production of mRNA transcribed from a gene or a protein product encoded by the gene. A differentially expressed gene may be overexpressed or underexpressed as compared to the expression level of a normal or control cell. In one aspect, it includes a differential that is 2.5 times, preferably 5 times or preferably 10 times higher or lower than the expression level detected in a control sample. The term "differentially expressed" also includes nucleotide sequences in a cell or tissue which are expressed where silent in a control cell or not expressed where expressed in a control cell.

The term "polypeptide" includes a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

"Hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". The stringency of a hybridization reaction includes the difficulty with which any two nucleic acid molecules will hybridize to one another. Under stringent conditions, nucleic acid molecules at least 60%, 65%, 70%, 75% identical to each other remain hybridized to each other, whereas molecules with low percent identity cannot remain hybridized. A preferred, non-limiting example of highly stringent hybridization conditions are hybridization in 6×sodium chloride/sodium citrate (SSC) at about 45° C., followed by one or more washes in 0.2×SSC, 0.1% SDS at 50° C., preferably at 55° C., more preferably at 60° C., and even more preferably at 65° C.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to hydrogen bond with each other, according to generally accepted base-pairing rules.

An "antibody" includes an immunoglobulin molecule capable of binding an epitope present on an antigen. As used herein, the term encompasses not only intact immunoglobulin molecules such as monoclonal and polyclonal antibodies, but also anti-idiotypic antibodies, mutants, fragments, fusion proteins, bi-specific antibodies, humanized proteins, and modifications of the immunoglobulin molecule that comprises an antigen recognition site of the required specificity.

As used herein, the term "prostate cancer" (CaP) refers to the art recognized use of the term which commonly appears in men. The term "prostate cancer" refers to both the appearance of a palpable tumor of the prostate, and also to microscopically detectable neoplastic or transformed cells in the prostate gland. In the latter case, the said cytologically-detectable prostate cancer may be asymptomatic, in that neither the patient nor the medical practitioner detects the presence of the cancer cells. Cancer cells are generally found in the prostates of men who live into their seventies or eighties, however not all of these men develop prostate cancer. In the event that prostate cancer metastasizes to additional sites distal to the prostate, the condition is described as metastatic cancer (MC), to distinguish this condition from organ-confined prostate cancer. CaP fatality results from metastatic dissemination of prostatic adenocarcinoma cells to distant sites, usually in the axial skeleton.

As used herein, the term "marker" includes a polynucleotide or polypeptide molecule which is present or absent, or increased or decreased in quantity or activity in subjects afflicted with prostate cancer, or in cells involved in prostate cancer. The relative change in quantity or activity of the marker is correlated with the incidence or risk of incidence of prostate cancer.

As used herein, the term "panel of markers" includes a group of markers, the quantity or activity of each member of which is correlated with the incidence or risk of incidence of prostate cancer. In certain embodiments, a panel of markers may include only those markers which are either increased or decreased in quantity or activity in subjects afflicted with or cells involved in prostate cancer. In other embodiments, a panel of markers may include only those markers present in a specific tissue type which are correlated with the incidence or risk of incidence of prostate cancer.

Various aspects of the invention are described in further detail in the following subsections:

I. Isolated Nucleic Acid Molecules

One aspect of the invention pertains to isolated nucleic acid molecules that either themselves are the genetic markers (e.g., mRNA) of the invention, or which encode the polypeptide markers of the invention, or fragments thereof. Another aspect of the invention pertains to isolated nucleic acid fragments sufficient for use as hybridization probes to identify the nucleic acid molecules encoding the markers of the invention in a sample, as well as nucleotide fragments for use as PCR primers for the amplification or mutation of the nucleic acid molecules which encode the markers of the invention. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated marker nucleic acid molecule of the invention, or nucleic acid molecule encoding a polypeptide marker of the invention, can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of the FKBP gene, e.g., the FKBP54 gene or a portion thereof, can be isolated using standard molecular biology techniques and the sequence information provided herein. Using all or portion of the nucleic acid sequence of the FKBP gene, e.g., the FKBP54 as a hybridization probe, a marker gene of the invention or a nucleic acid molecule encoding a polypeptide marker of the invention can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

A nucleic acid of the invention can be amplified using cDNA, MRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to marker nucleotide sequences, or nucleotide sequences encoding a marker of the invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence of a marker of the invention i.e., FKBP54, or a portion of any of these nucleotide sequences. A nucleic acid molecule which is complementary to such a nucleotide sequence is one which is sufficiently complementary to the nucleotide sequence such that it can hybridize to the nucleotide sequence, thereby forming a stable duplex.

The nucleic acid molecule of the invention, moreover, can comprise only a portion of the nucleic acid sequence of a marker nucleic acid of the invention, or a gene encoding a marker polypeptide of the invention, for example, a fragment which can be used as a probe or primer. The probe/primer typically comprises substantially purified oligonucleotide. The oligonucleotide typically comprises a region of nucleotide sequence that hybridizes under stringent conditions to at least about 7 or 15, preferably about 20 or 25, more preferably about 50, 75, 100, 125, 150, 175, 200, 225, 250, 275, 300, 325, 350, 400 or more consecutive nucleotides of a marker nucleic acid, or a nucleic acid encoding a marker polypeptide of the invention.

Probes based on the nucleotide sequence of a marker gene or of a nucleic acid molecule encoding a marker polypeptide of the invention can be used to detect transcripts or genomic sequences corresponding to the marker gene(s) and/or marker polypeptide(s) of the invention. In preferred embodiments, the probe comprises a label group attached thereto, e.g., the label group can be a radioisotope, a fluorescent compound, an enzyme, or an enzyme co-factor. Such probes can be used as a part of a diagnostic test kit for identifying cells or tissue which misexpress (e.g., over- or under-express) a marker polypeptide of the invention, or which have greater or fewer copies of a marker gene of the invention. For example, a level of a marker polypeptide-encoding nucleic acid in a sample of cells from a subject may be detected, the amount of mRNA transcript of a gene encoding a marker polypeptide may be determined, or the presence of mutations or deletions of a marker gene of the invention may be assessed.

The invention further encompasses nucleic acid molecules that differ from the nucleic acid sequences of the FKBP gene, e.g., FKBP54 gene due to degeneracy of the genetic code and which thus encode the same proteins as those encoded by the FKBP gene, e.g., FKBP54 gene.

In addition to the nucleotide sequences of the FKBP gene, e.g., FKBP54 gene it will be appreciated by those skilled in the art that DNA sequence polymorphisms that lead to changes in the amino acid sequences of the proteins encoded by the FKBP gene, e.g., FKBP54 gene may exist within a population (e.g., the human population). Such genetic polymorphism in the FKBP gene, e.g., FKBP54 gene may exist among individuals within a population due to natural allelic variation. An allele is one of a group of genes which occur alternatively at a given genetic locus. In addition it will be appreciated that DNA polymorphisms that affect RNA expression levels can also exist that may affect the overall expression level of that gene (e.g., by affecting regulation or degradation). As used herein, the phrase "allelic variant" includes a nucleotide sequence which occurs at a given locus or to a polypeptide encoded by the nucleotide sequence. As used herein, the terms "gene" and "recombinant gene" refer to nucleic acid molecules which include an open reading frame encoding a marker polypeptide of the invention.

Nucleic acid molecules corresponding to natural allelic variants and homologues of the FKBP gene, e.g., FKBP54 marker gene, or genes encoding the FKBP, e.g., FKBP54 marker protein of the invention can be isolated based on their homology to the FKBP genes, e.g., FKBP54 gene using the cDNAs disclosed herein, or a portion thereof, as a hybridization probe according to standard hybridization techniques under stringent hybridization conditions. Nucleic acid molecules corresponding to natural allelic variants and homologues of the marker genes of the invention can further be isolated by mapping to the same chromosome or locus as the marker genes or genes encoding the marker proteins of the invention.

In another embodiment, an isolated nucleic acid molecule of the invention is at least 15, 20, 25, 30, 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000 or more nucleotides in length and hybridizes under stringent conditions to a nucleic acid molecule corresponding to a nucleotide sequence of a marker gene or gene encoding a marker protein of the invention. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50° C., preferably at 55° C., more preferably at 60° C., and even more preferably at 65° C. Preferably, an isolated nucleic acid molecule of the invention that hybridizes under stringent conditions to the sequence of the FKBP gene, e.g., FKBP54 gene. As used herein, a "naturally-occurring" nucleic acid molecule includes an RNA or DNA molecule having a nucleotide sequence that occurs in nature (e.g. encodes a natural protein).

In addition to naturally-occurring allelic variants of the marker gene and gene encoding a marker protein of the invention sequences that may exist in the population, the skilled artisan will further appreciate that changes can be introduced by mutation into the nucleotide sequences of the marker genes or genes encoding the marker proteins of the invention, thereby leading to changes in the amino acid sequence of the encoded proteins, without altering the functional activity of these proteins. For example, nucleotide substitutions leading to amino acid substitutions at "nonessential" amino acid residues can be made. A "nonessential" amino acid residue is a residue that can be altered from the wild-type sequence of a protein without altering the biological activity, whereas an "essential" amino acid residue is required for biological activity. For example, amino acid residues that are conserved among allelic variants or homologs of a gene (e.g., among homologs of a gene from different species) are predicted to be particularly unamenable to alteration.

Accordingly, another aspect of the invention pertains to nucleic acid molecules encoding a marker protein of the invention that contain changes in amino acid residues that are not essential for activity. Such proteins differ in amino acid sequence from the marker proteins encoded by the FKBP genes, e.g., the FKBP54 gene, yet retain biological activity. In one embodiment, the protein comprises an amino acid sequence at least about 60%, 65%, 70%, 75%, 80%, 85%, 90%, 95%, 98% or more homologous to a marker protein of the invention.

An isolated nucleic acid molecule encoding a protein homologous to a marker protein of the invention can be created by introducing one or more nucleotide substitutions, additions or deletions into the nucleotide sequence of the gene encoding the marker protein, such that one or more amino acid substitutions, additions or deletions are introduced into the encoded protein. Mutations can be introduced into the FKBP gene, e.g., the FKBP54 gene of the invention by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of a coding sequence of a gene of the invention, such as by saturation mutagenesis, and the resultant mutants can be screened for biological activity to identify mutants that retain activity. Following mutagenesis, the encoded protein can be expressed recombinantly and the activity of the protein can be determined.

Another aspect of the invention pertains to isolated nucleic acid molecules which are antisense to the marker genes and genes encoding marker proteins of the invention. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand of the FKBP gene, e.g., the FKBP54 gene, or to only a portion thereof. In one embodiment, an antisense nucleic acid molecule is antisense to a "coding region" of the coding strand of a nucleotide sequence of the invention. The term "coding region" includes the region of the nucleotide sequence comprising codons which are translated into amino acid. In another embodiment, the antisense nucleic acid molecule is antisense to a "noncoding region" of the coding strand of a nucleotide sequence of the invention. The term "noncoding region" includes 5' and 3' sequences which flank the coding region that are not translated into amino acids (i.e., also referred to as 5' and 3' untranslated regions).

Antisense nucleic acids of the invention can be designed according to the rules of Watson and Crick base pairing. The antisense nucleic acid molecule can be complementary to the entire coding region of an mRNA corresponding to a gene of the invention, but more preferably is an oligonucleotide which is antisense to only a portion of the coding or noncoding region. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a marker protein of the invention to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site (e.g., in skin). Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave mRNA transcripts of the FKBP54 gene of the invention, to thereby inhibit translation of this mRNA. A ribozyme having specificity for a marker protein-encoding nucleic acid can be designed based upon the nucleotide sequence of a gene of the invention, disclosed herein. For example, a derivative of a Tetrahymena L-19 IVS RNA can be constructed in which the nucleotide sequence of the active site is complementary to the nucleotide sequence to be cleaved in a marker protein-encoding mRNA. See, e.g., Cech et al. U.S. Pat. No. 4,987,071; and Cech et al. U.S. Pat. No. 5,116,742. Alternatively, mRNA transcribed from a gene of the invention can be used to select a catalytic RNA having a specific ribonuclease activity from a pool of RNA molecules. See, e.g., Bartel, D. and Szostak, J. W. (1993) *Science* 261:1411–1418.

Alternatively, expression of FKBP genes, e.g., the FKBP54 gene can be inhibited by targeting nucleotide sequences complementary to the regulatory region of these genes (e.g., the promoter and/or enhancers) to form triple helical structures that prevent transcription of the gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

In yet another embodiment, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs can be used in therapeutic and diagnostic applications. For example, PNAs can be used as antisense or antigene agents for sequence-specific modulation of gene expression by, for example, inducing transcription or translation arrest or inhibiting replication. PNAs of the nucleic acid molecules of FKBPs, e.g., FKBP54 can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of the nucleic acid molecules of the invention can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, eg., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent). Finally, the oligonucleotide may be detectably labeled, either such that the label is detected by the addition of another reagent (e.g. a substrate for an enzymatic label), or is detectable immediately upon hybridization of the nucleotide (e.g., a radioactive label or a fluorescent label (e.g., a molecular beacon, as described in U.S. Pat. No. 5,876,930.

II. Isolated Proteins and Antibodies

One aspect of the invention pertains to isolated marker proteins, and biologically active portions thereof, as well as polypeptide fragments suitable for use as immunogens to raise anti-marker protein antibodies. In one embodiment, native marker proteins can be isolated from cells or tissue sources by an appropriate purification scheme using standard protein purification techniques. In another embodiment, marker proteins are produced by recombinant DNA techniques. Alternative to recombinant expression, a marker protein or polypeptide can be synthesized chemically using standard peptide synthesis techniques.

An "isolated" or "purified" protein or biologically active portion thereof is substantially free of cellular material or other contaminating proteins from the cell or tissue source from which the marker protein is derived, or substantially free from chemical precursors or other chemicals when chemically synthesized. The language "substantially free of cellular material" includes preparations of marker protein in which the protein is separated from cellular components of the cells from which it is isolated or recombinantly produced. In one embodiment, the language "substantially free of cellular material" includes preparations of marker protein having less than about 30% (by dry weight) of non-marker protein (also referred to herein as a "contaminating protein"), more preferably less than about 20% of non-marker protein, still more preferably less than about 10% of non-marker protein, and most preferably less than about 5% non-marker protein. When the marker protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of marker protein in which the protein is separated from chemical precursors or other chemicals which are involved in the synthesis of the protein. In one embodiment, the language "substantially free of chemical precursors or other chemicals" includes preparations of protein having less than about 30% (by dry weight) of chemical precursors or non-protein chemicals, more preferably less than about 20% chemical precursors or non-protein chemicals, still more preferably less than about 10% chemical precursors or non-protein chemicals, and most preferably less than about 5% chemical precursors or non-protein chemicals.

As used herein, a "biologically active portion" of a marker protein includes a fragment of a marker protein comprising amino acid sequences sufficiently homologous to or derived from the amino acid sequence of the marker protein, which include fewer amino acids than the full length marker proteins, and exhibit at least one activity of a marker protein. Typically, biologically active portions comprise a domain or motif with at least one activity of the marker protein. A biologically active portion of a marker protein can be a polypeptide which is, for example, 10, 25, 50, 100, 200 or more amino acids in length. Biologically active portions of a marker protein can be used as targets for developing agents which modulate a marker protein-mediated activity.

In a preferred embodiment, marker protein is encoded by the FKBP genes, e.g., FKBP54 gene. In other embodiments, the marker protein is substantially homologous to a marker protein encoded by the FKBP genes, e.g., FKBP54 gene, and retains the functional activity of the marker protein, yet differs in amino acid sequence due to natural allelic variation or mutagenesis, as described in detail in subsection I above. Accordingly, in another embodiment, the marker protein is a protein which comprises an amino acid sequence at least about 60%, 65%, 70%, 75%, 80%, 85%, 90%, 95%, 98% or more homologous to the amino acid sequence encoded by the FKBP genes, e.g., FKBP54 gene.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mat. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to marker protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used.

The invention also provides chimeric or fusion marker proteins. As used herein, a marker "chimeric protein" or "fusion protein" comprises a marker polypeptide operatively linked to a non-marker polypeptide. An "marker polypeptide" includes a polypeptide having an amino acid sequence encoded by the FKBP genes, e.g., FKBP54 gene, whereas a "non-marker polypeptide" includes a polypeptide having an amino acid sequence corresponding to a protein which is not substantially homologous to the marker protein, e.g., a protein which is different from marker protein and which is derived from the same or a different organism. Within a marker fusion protein the polypeptide can correspond to all or a portion of a marker protein. In a preferred embodiment, a marker fusion protein comprises at least one biologically active portion of a marker protein. Within the fusion protein, the term "operatively linked" is intended to indicate that the marker polypeptide and the non-marker polypeptide are fused in-frame to each other. The non-marker polypeptide can be fused to the N-terminus or C-terminus of the marker polypeptide.

For example, in one embodiment, the fusion protein is a GST-marker fusion protein in which the marker sequences are fused to the C-terminus of the GST sequences. Such fusion proteins can facilitate the purification of recombinant marker proteins.

In another embodiment, the fusion protein is a marker protein containing a heterologous signal sequence at its N-terminus. In certain host cells (e.g., mammalian host cells), expression and/or secretion of marker proteins can be increased through use of a heterologous signal sequence. Such signal sequences are well known in the art.

The marker fusion proteins of the invention can be incorporated into pharmaceutical compositions and administered to a subject in vivo, as described herein. The marker fusion proteins can be used to affect the bioavailability of a marker protein substrate. Use of marker fusion proteins may be useful therapeutically for the treatment of disorders (e.g., prostate cancer) caused by, for example, (i) aberrant modification or mutation of a gene encoding a markerprotein; (ii) mis-regulation of the marker protein-encoding gene; and (iii) aberrant post-translational modification of a marker protein.

Moreover, the marker-fusion proteins of the invention can be used as immunogens to produce anti-marker protein antibodies in a subject, to purify marker protein ligands and in screening assays to identify molecules which inhibit the interaction of a marker protein with a marker protein substrate.

Preferably, a marker chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A marker protein-encoding nucleic acid can be cloned into such an expression vector such that the fusion moiety is linked in-frame to the marker protein.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the marker proteins of the invention which function as either agonists (mimetics) or as antagonists to the marker proteins. Variants of the marker proteins can be generated by mutagenesis, e.g., discrete point mutation or truncation of a marker protein. An agonist of the marker proteins can retain substantially the same, or a subset, of the biological activities of the naturally occurring form of a marker protein. An antagonist of a marker protein can inhibit one or more of the activities of the naturally occurring form of the marker protein by, for example, competitively modulating an activity of a marker protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the marker protein.

Variants of a marker protein which function as either marker protein agonists (mimetics) or as marker protein antagonists can be identified by screening combinatorial libraries of mutants, e.g., truncation mutants, of a marker protein for marker protein agonist or antagonist activity. In one embodiment, a variegated library of marker protein variants is generated by combinatorial mutagenesis at the nucleic acid level and is encoded by a variegated gene library. A variegated library of marker protein variants can be produced by, for example, enzymatically ligating a mixture of synthetic oligonucleotides into gene sequences such that a degenerate set of potential marker protein sequences is expressible as individual polypeptides, or alternatively, as a set of larger fusion proteins (e.g., for phage display) containing the set of marker protein sequences therein. There are a variety of methods which can be used to produce libraries of potential marker protein variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential marker protein sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a protein coding sequence corresponding to a marker protein of the invention can be used to generate a variegated population of marker protein fragments for screening and subsequent selection of variants of a marker protein. In one embodiment, a library of coding sequence fragments can be generated by treating a double stranded PCR fragment of a marker protein coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the marker protein.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify marker variants (Arkin and Yourvan (1992) *Proc. Natl. Acad. Sci. USA* 89:7811–7815; Delgrave et al. (1993) *Protein Engineering* 6(3):327–331).

An isolated marker protein, or a portion or fragment thereof, can be used as an immunogen to generate antibodies that bind marker proteins using standard techniques for polyclonal and monoclonal antibody preparation. A full-length marker protein can be used or, alternatively, the invention provides antigenic peptide fragments of these proteins for use as immunogens. The antigenic peptide of a marker protein comprises at least 8 amino acid residues of an amino acid sequence encoded by the FKBP54 gene, and encompasses an epitope of a marker protein such that an antibody raised against the peptide forms a specific immune complex with the marker protein. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of the marker protein that are located on the surface of the protein, e.g., hydrophilic regions, as well as regions with high antigenicity.

A marker protein immunogen typically is used to prepare antibodies by immunizing a suitable subject, (e.g., rabbit, goat, mouse or other mammal) with the immunogen. An appropriate immunogenic preparation can contain, for example, recombinantly expressed marker protein or a chemically synthesized marker polypeptide. The preparation can further include an adjuvant, such as Freund's complete or incomplete adjuvant, or similar immunostimulatory agent. Immunization of a suitable subject with an immunogenic marker protein preparation induces a polyclonal anti-marker protein antibody response.

Accordingly, another aspect of the invention pertains to anti-marker protein antibodies. The term "antibody" as used herein includes immunoglobulin molecules and immunologically active portions of immunoglobulin molecules, i.e., molecules that contain an antigen binding site which specifically binds (immunoreacts with) an antigen, such as a marker protein. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to marker proteins. The term "monoclonal antibody" or "monoclonal antibody composition", as used herein, includes a population of antibody molecules that contain only one species of an antigen binding site capable of immunoreacting with a particular epitope. A monoclonal antibody composition thus typically displays a single binding affinity for a particular marker protein with which it immunoreacts.

Polyclonal anti-marker protein antibodies can be prepared as described above by immunizing a suitable subject with a marker protein of the invention. The anti-marker protein antibody titer in the immunized subject can be monitored over time by standard techniques, such as with an enzyme linked immunosorbent assay (ELISA) using immobilized marker protein. If desired, the antibody molecules directed against marker proteins can be isolated from the mammal (e g., from the blood) and further purified by well known techniques, such as protein A chromatography, to obtain the IgG fraction. At an appropriate time after immunization, e.g., when the anti-marker protein antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques.

The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.,* 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a marker protein immunogen as described above, and the culture supernatants of the resulting hybridoma cells are screened to identify a hybridoma producing a monoclonal antibody that binds to a marker protein of the invention.

Any of the many well known protocols used for fusing lymphocytes and immortalized cell lines can be applied for the purpose of generating an anti-marker protein monoclonal antibody (see, e.g., G. Galfre et al. (1977) *Nature* 266:55052; Gefter et al. *Somatic Cell Genet.*, cited supra; Lerner, Yale *J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line.

Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind to a marker protein, e.g., using a standard ELISA assay.

Alternative to preparing monoclonal antibody-secreting hybridomas, a monoclonal anti-marker protein antibody can be identified and isolated by screening a recombinant combinatorial immunoglobulin library (e.g., an antibody phage display library) with marker protein to thereby isolate immunoglobulin library members that bind to a marker protein. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-marker protein antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559);

Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human subjects. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899–903).

An anti-marker protein antibody (e.g., monoclonal antibody) can be used to isolate a marker protein of the invention by standard techniques, such as affinity chromatography or immunoprecipitation. An anti-marker protein antibody can facilitate the purification of natural marker proteins from cells and of recombinantly produced marker proteins expressed in host cells. Moreover, an anti-marker protein antibody can be used to detect marker protein (e.g., in a cellular lysate or cell supernatant) in order to evaluate the abundance and pattern of expression of the marker protein. Anti-marker protein antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a marker protein of the invention (or a portion thereof). As used herein, the term "vector" includes a nucleic acid molecule capable of transporting another nucleic acid to which it has been linked. One type of vector is a "plasmid", which includes a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g. replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., marker proteins, mutant forms of marker proteins, fusion proteins, and the like).

The recombinant expression vectors of the invention can be designed for expression of marker proteins in prokaryotic or eukaryotic cells. For example, marker proteins can be expressed in bacterial cells such as *E. coli*, insect cells (using baculovirus expression vectors) yeast cells or mammalian cells. Suitable host cells are discussed further in Goeddel,

*Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in marker activity assays, (e.g., direct assays or competitive assays described in detail below), or to generate antibodies specific for marker proteins, for example.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gnl). This viral polymerase is supplied by host strains BL21(DE3) or HMS174 (DE3) from a resident prophage harboring a T7 gnl gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the marker protein expression vector is a yeast expression vector. Examples of vectors for expression in yeast *S. cerevisiae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, marker proteins of the invention can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed.,* Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the □-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to mRNA corresponding to the FKBP54 gene. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a nucleic acid molecule of the invention is introduced, e.g., FKBP genes, such as the FKBP54 gene within a recombinant expression vector or a nucleic acid molecule of the invention containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a marker protein of the invention can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a marker protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a marker protein. Accordingly, the invention further provides methods for producing a marker protein using the host cells of the invention. In one embodiment, the method comprises culturing the host cell of invention (into which a recombinant expression vector encoding a marker protein has been introduced) in a suitable medium such that a marker protein of the invention is produced. In another embodiment, the method further comprises isolating a marker protein from the medium or the host cell. The host cells of the invention can also be used to produce non-human transgenic animals. For example, in one embodiment, a host cell of the invention is a fertilized oocyte or an embryonic stem cell into which marker-protein-coding sequences have been introduced. Such host cells can then be used to create non-human transgenic animals in which exogenous sequences encoding a marker protein of the invention have been introduced into their genome or homologous recombinant animals in which endogenous sequences encoding the marker proteins of the invention have been altered. Such animals are useful for studying the function and/or activity of a marker protein and for identifying and/or evaluating modulators of marker protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous FKBP54 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a marker-encoding nucleic acid into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to a transgene to direct expression of a marker protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a transgene of the invention in its genome and/or expression of mRNA corresponding to a gene of the invention in tissues or cells of the animals. A transgenic founder animal can then be used to breed additional animals carrying the transgene. Moreover, transgenic animals carrying a transgene encoding a marker protein can further be bred to other transgenic animals carrying other transgenes.

To create a homologous recombinant animal, a vector is prepared which contains at least a portion of a gene of the invention into which a deletion, addition or substitution has been introduced to thereby alter, e.g., functionally disrupt, the gene. The gene can be a human gene, but more preferably, is a non-human homologue of a human FKBP, e.g., FKBP54. For example, a mouse gene can be used to construct a homologous recombination nucleic acid molecule, e.g., a vector, suitable for altering an endogenous gene of the invention in the mouse genome. In a preferred embodiment, the homologous recombination nucleic acid molecule is designed such that, upon homologous recombination, the endogenous gene of the invention is functionally disrupted (i.e., no longer encodes a functional protein; also referred to as a "knock out" vector). Alternatively, the homologous recombination nucleic acid molecule can be designed such that, upon homologous recombination, the endogenous gene is mutated or otherwise altered but still encodes functional protein (e.g., the upstream regulatory region can be altered to thereby alter the expression of the endogenous marker protein). In the homologous recombination nucleic acid molecule, the altered portion of the gene of the invention is flanked at its 5' and 3' ends by additional nucleic acid sequence of the gene of the invention to allow for homologous recombination to occur between the exogenous gene carried by the homologous recombination nucleic acid molecule and an endogenous gene in a cell, e.g., an embryonic stem cell. The additional flanking nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) Cell 51–503 for a description of homologous recombination vectors). The homologous recombination nucleic acid molecule is introduced into a cell, e.g., an embryonic stem cell line (e.g., by electroporation) and cells in which the introduced gene has homologously recombined with the endogenous gene are selected (see e.g., Li, E. et al. (1992) Cell 69:915). The selected cells can then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) Current Opinion in Biotechnology 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of Saccharomyces cerevisiae (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) Nature 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The nucleic acid molecules of the invention i.e. FKBP54, fragments of marker proteins, and anti-marker protein antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid corresponding to a marker of the invention. Such methods comprise formulating a pharmaceutically acceptable carrier with an agent which modulates expression or activity of a polypeptide or nucleic acid corresponding to a marker of the invention. Such compositions can further include additional active agents. Thus, the invention further includes methods for preparing a pharmaceutical composition by formulating a pharmaceutically acceptable carrier with an agent which modulates expression or activity of a polypeptide or nucleic acid corresponding to a marker of the invention and one or more additional active compounds.

The invention also provides methods (also referred to herein as "screening assays") for identifying modulators, i.e., candidate or test compounds or agents (e.g. peptides, peptidomimetics, peptoids, small molecules or other drugs) which (a) bind to the marker, or (b) have a modulatory (e.g., stimulatory or inhibitory) effect on the activity of the marker or, more specifically, (c) have a modulatory effect on the interactions of the marker with one or more of its natural substrates (e.g., peptide, protein, hormone, co-factor, or nucleic acid), or (d) have a modulatory effect on the expression of the marker. Such assays typically comprise a reaction between the marker and one or more assay components. The other components may be either the test compound itself, or a combination of test compound and a natural binding partner of the marker.

The test compounds of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, J. Med. Chem. 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradennal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifingal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a marker protein or an anti-marker protein antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein includes physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Computer Readable Means and Arrays

Computer readable media comprising a marker(s) of the present invention is also provided. As used herein, "computer readable media" includes a medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. The skilled artisan will readily appreciate how any of the presently known computer readable mediums can be used to create a manufacture comprising computer readable medium having recorded thereon a marker of the present invention.

As used herein, "recorded" includes a process for storing information on computer readable medium. Those skilled in the art can readily adopt any of the presently known methods for recording information on computer readable medium to generate manufactures comprising the markers of the present invention.

A variety of data processor programs and formats can be used to store the marker information of the present invention on computer readable medium. For example, the nucleic acid sequence corresponding to the markers can be represented in a word processing text file, formatted in commercially-available software such as WordPerfect and MicroSoft Word, or represented in the form of an ASCII file, stored in a database application, such as DB2, Sybase, Oracle, or the like. Any number of dataprocessor structuring formats (e.g. text file or database) may be adapted in order to obtain computer readable medium having recorded thereon the markers of the present invention.

By providing the markers of the invention in computer readable form, one can routinely access the marker sequence information for a variety of purposes. For example, one skilled in the art can use the nucleotide or amino acid sequences of the invention in computer readable form to compare a target sequence or target structural motif with the sequence information stored within the data storage means. Search means are used to identify fragments or regions of the sequences of the invention which match a particular target sequence or target motif.

The invention also includes an array comprising a marker (s) of the present invention. The array can be used to assay expression of one or more genes in the array. In one embodiment, the array can be used to assay gene expression in a tissue to ascertain tissue specificity of genes in the array. In this manner, up to about 8600 genes can be simultaneously assayed for expression. This allows a profile to be developed showing a battery of genes specifically expressed in one or more tissues.

In addition to such qualitative determination, the invention allows the quantitation of gene expression. Thus, not only tissue specificity, but also the level of expression of a battery of genes in the tissue is ascertainable. Thus, genes can be grouped on the basis of their tissue expression per se and level of expression in that tissue. This is useful, for example, in ascertaining the relationship of gene expression between or among tissues. Thus, one tissue can be perturbed and the effect on gene expression in a second tissue can be determined. In this context, the effect of one cell type on another cell type in response to a biological stimulus can be determined. Such a determination is useful, for example, to know the effect of cell-cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development and differentiation, disease progression, in vitro processes, such a cellular transformation and senescence, autonomic neural and neurological processes, such as, for example, pain and appetite, and cognitive functions, such as learning or memory.

The array is also useful for ascertaining the effect of the expression of a gene on the expression of other genes in the same cell or in different cells. This provides, for example, for a selection of alternate molecular targets for therapeutic intervention if the ultimate or downstream target cannot be regulated.

The array is also useful for ascertaining differential expression patterns of one or more genes in normal and diseased cells. This provides a battery of genes that could serve as a molecular target for diagnosis or therapeutic intervention.

VI. Predictive Medicine

The present invention pertains to the field of predictive medicine in which diagnostic assays, prognostic assays, pharmacogenetics and monitoring clinical trials are used for prognostic (predictive) purposes to thereby treat an individual prophylactically. Accordingly, one aspect of the present invention relates to diagnostic assays for determining marker protein and/or nucleic acid expression as well as marker protein activity, in the context of a biological sample (e.g., blood, serum, cells, tissue) to thereby determine whether an individual is afflicted with a disease or disorder, or is at risk of developing a disorder, associated with increased or decreased marker protein expression or activity. The invention also provides for prognostic (or predictive) assays for determining whether an individual is at risk of developing a disorder associated with marker protein, nucleic acid expression or activity. For example, the number of copies of a marker gene can be assayed in a biological sample. Such assays can be used for prognostic or predictive purposes to thereby phophylactically treat an individual prior to the onset of a disorder (e.g., prostate cancer) characterized by or associated with marker protein, nucleic acid expression or activity.

Another aspect of the invention pertains to monitoring the influence of agents (e.g., drugs, compounds) on the expression or activity of marker in clinical trials.

These and other agents are described in further detail in the following sections.

1. Diagnostic Assays

An exemplary method for detecting the presence or absence of marker protein or nucleic acid of the invention in a biological sample involves obtaining a biological sample from a test subject and contacting the biological sample with a compound or an agent capable of detecting the protein or nucleic acid (e.g., mRNA, genomic DNA) that encodes the marker protein such that the presence of the marker protein or nucleic acid is detected in the biological sample. A preferred agent for detecting mRNA or genomic DNA corresponding to a marker gene or protein of the invention is a labeled nucleic acid probe capable of hybridizing to a mRNA or genomic DNA of the invention. Suitable probes for use in the diagnostic assays of the invention are described herein.

A preferred agent for detecting marker protein is an antibody capable of binding to marker protein, preferably an antibody with a detectable label. Antibodies can be polyclonal, or more preferably, monoclonal. An intact antibody, or a fragment thereof (eg., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect marker mRNA, protein, or genomic DNA in a biological sample in vitro as well as in vivo. For example, in vitro techniques for detection of marker mRNA include Northern hybridizations and in situ hybridizations. In vitro techniques for detection of marker protein include enzyme linked immunosorbent assays (ELISAs), Western blots, immunoprecipitations and immunofluorescence. In vitro techniques for detection of marker genomic DNA include Southern hybridizations. Furthermore, in vivo techniques for detection of marker protein include introducing into a subject a labeled anti-marker antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample (e.g., non-prostate cancer cells sample) from a control subject, contacting the control sample with a compound or agent capable of detecting marker protein, mRNA, or genomic DNA, such that the presence of marker protein, mRNA or genomic DNA is detected in the biological sample, and comparing the presence of marker protein, mRNA or genomic DNA in the control sample with the presence of marker protein, mRNA or genomic DNA in the test sample.

The invention also encompasses kits for detecting the presence of marker in a biological sample. For example, the kit can comprise a labeled compound or agent capable of detecting marker protein or mRNA in a biological sample; means for determining the amount of marker in the sample; and means for comparing the amount of marker in the sample with a standard. The compound or agent can be packaged in a suitable container. The kit can further comprise instructions for using the kit to detect marker protein or nucleic acid.

2. Prognostic Assays

The diagnostic methods described herein can furthermore be utilized to identify subjects having or at risk of developing a disease or disorder associated with aberrant marker expression or activity. As used herein, the term "aberrant" includes a marker expression or activity which deviates from the wild type marker expression or activity. Aberrant expression or activity includes increased or decreased expression or activity, as well as expression or activity which does not follow the wild type developmental pattern of expression or the subcellular pattern of expression. For example, aberrant marker expression or activity is intended to include the cases in which a mutation in the marker gene causes the marker gene to be under-expressed or over-expressed and situations in which such mutations result in a non-functional marker protein or a protein which does not function in a wild-type fashion, e.g., a protein which does not interact with a marker ligand or one which interacts with a non-marker protein ligand.

The assays described herein, such as the preceding diagnostic assays or the following assays, can be utilized to identify a subject having or at risk of developing a disorder associated with a misregulation in marker protein activity or nucleic acid expression, such as prostate cancer. Alternatively, the prognostic assays can be utilized to identify a subject having or at risk for developing a disorder associated with a misregulation in marker protein activity or nucleic acid expression, such as prostate cancer. Thus, the present invention provides a method for identifying a disease or disorder associated with aberrant marker expression or activity in which a test sample is obtained from a subject and marker protein or nucleic acid (e.g., mRNA or genomic DNA) is detected, wherein the presence of marker protein or nucleic acid is diagnostic for a subject having or at risk of developing a disease or disorder associated with aberrant marker expression or activity. As used herein, a "test sample" includes a biological sample obtained from a subject of interest. For example, a test sample can be a biological fluid (e.g., blood), cell sample, or tissue (e.g. skin).

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with increased or decreased marker expression or activity. For example, such methods can be used to determine whether a subject can be effectively treated with an agent for a disorder such as prostate cancer. Thus, the present invention provides methods for determining whether a subject can be effectively treated with an agent for a disorder associated with increased or decreased marker expression or activity in which a test sample is obtained and marker protein or nucleic acid expression or activity is detected (e.g., wherein the abundance of marker protein or nucleic acid expression or activity is diagnostic for a subject that can be administered the agent to treat a disorder associated with increased or decreased marker expression or activity).

The methods of the invention can also be used to detect genetic alterations in a marker gene, thereby determining if a subject with the altered gene is at risk for a disorder characterized by misregulation in marker protein activity or nucleic acid expression, such as prostate cancer. In preferred embodiments, the methods include detecting, in a sample of cells from the subject, the presence or absence of a genetic alteration characterized by at least one of an alteration affecting the integrity of a gene encoding a marker-protein, or the mis-expression of the marker gene. For example, such genetic alterations can be detected by ascertaining the existence of at least one of 1) a deletion of one or more nucleotides from a marker gene; 2) an addition of one or more nucleotides to a marker gene; 3) a substitution of one or more nucleotides of a marker gene, 4) a chromosomal rearrangement of a marker gene; 5) an alteration in the level of a messenger RNA transcript of a marker gene, 6) aberrant modification of a marker gene, such as of the methylation pattern of the genomic DNA, 7) the presence of a non-wild type splicing pattern of a messenger RNA transcript of a marker gene, 8) a non-wild type level of a marker-protein, 9) allelic loss of a marker gene, and 10) inappropriate post-translational modification of a marker-protein. As described herein, there are a large number of assays known in the art which can be used for detecting alterations in a marker gene. A preferred biological sample is a tissue (e.g., skin) or blood sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the marker-gene (see Abravaya et al. (1995) *Nucleic Acids Res* .23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a marker gene under conditions such that hybridization and amplification of the marker-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a marker gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in a marker gene or a gene encoding a marker protein of the invention can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in marker can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the marker gene and detect mutations by comparing the sequence of the sample marker with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g. PCT International Publication No. WO 94/16101; Cohen et al. (1996) *Adv. Chromatogr.* 36:127–162; and Griffin et al. (1993) *Appl. Bioch em. Biotechnol.* 38:147–159).

Other methods for detecting mutations in the marker gene or gene encoding a marker protein of the invention include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type marker sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in marker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a marker sequence, e.g., a wild-type marker sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in marker genes or genes encoding a marker protein of the invention. For example, single strand conformation polymorphism (SSCP) may be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control marker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose subjects exhibiting symptoms or family history of a disease or illness involving a marker gene.

Furthermore, any cell type or tissue in which marker is expressed may be utilized in the prognostic assays described herein.

3. Monitoring of Effects During Clinical Trials

Monitoring the influence of agents (e.g., drugs) on the expression or activity of a marker protein (e.g., the modulation of prostate cancer) can be applied not only in basic drug screening, but also in clinical trials. For example, the effectiveness of an agent determined by a screening assay as described herein to increase marker gene expression, protein levels, or upregulate marker activity, can be monitored in clinical trials of subjects exhibiting decreased marker gene expression, protein levels, or downregulated marker activity. Alternatively, the effectiveness of an agent determined by a screening assay to decrease marker gene expression, protein levels, or downregulate marker activity, can be monitored in clinical trials of subjects exhibiting increased marker gene expression, protein levels, or upregulated marker activity. In such clinical trials, the expression or activity of a marker gene, and preferably, other genes that have been implicated in, for example, a marker-associated disorder (e.g., prostate cancer) can be used as a "read out" or markers of the phenotype of a particular cell.

For example, and not by way of limitation, genes, including marker genes and genes encoding a marker protein of the invention, that are modulated in cells by treatment with an agent (e.g., compound, drug or small molecule) which modulates marker activity (e.g., identified in a screening assay as described herein) can be identified. Thus, to study the effect of agents on marker-associated disorders (e.g., prostate cancer), for example, in a clinical trial, cells can be isolated and RNA prepared and analyzed for the levels of expression of marker and other genes implicated in the marker-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of marker or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a marker protein, mRNA, or genomic DNA in the preadministration sample; (iii) obtaining one or more post-administration samples from the subject; (iv) detecting the level of expression or activity of the marker protein, mRNA, or genomic DNA in the post-administration samples; (v) comparing the level of expression or activity of the marker protein, mRNA, or genomic DNA in the pre-administration sample with the marker protein, mRNA, or genomic DNA in the post administration sample or samples; and (vi) altering the administration of the agent to the subject accordingly. For example, increased administration of the agent may be desirable to increase the expression or activity of marker to higher levels than detected, i.e., to increase the effectiveness of the agent. Alternatively, decreased administration of the agent may be desirable to decrease expression or activity of marker to lower levels than detected, i.e. to decrease the effectiveness of the agent. According to such an embodiment, marker expression or activity may be used as an indicator of the effectiveness of an agent, even in the absence of an observable phenotypic response.

4. Methods of Treatment

The present invention provides for both prophylactic and therapeutic methods of treating a subject at risk for (or susceptible to) a disorder or having a disorder associated with aberrant marker expression or activity. With regards to both prophylactic and therapeutic methods of treatment, such treatments may be specifically tailored or modified, based on knowledge obtained from the field of pharmacogenomics. "Pharmacogenomics", as used herein, includes the application of genomics technologies such as gene sequencing, statistical genetics, and gene expression analysis to drugs in clinical development and on the market. More specifically, the term refers the study of how a subject's genes determine his or her response to a drug (e.g., a subject's "drug response phenotype", or "drug response genotype".) Thus, another aspect of the invention provides methods for tailoring an individual's prophylactic or therapeutic treatment with either the marker molecules of the present invention or marker modulators according to that individual's drug response genotype. Pharmacogenomics allows a clinician or physician to target prophylactic or therapeutic treatments to subjects who will most benefit from the treatment and to avoid treatment of subjects who will experience toxic drug-related side effects.

5. Prophylactic Methods

In one aspect, the invention provides a method for preventing in a subject, a disease or condition (e.g., prostate cancer) associated with increased or decreased marker expression or activity, by administering to the subject a marker protein or an agent which modulates marker protein expression or at least one marker protein activity. Subjects at risk for a disease which is caused or contributed to by increased or decreased marker expression or activity can be identified by, for example, any or a combination of diagnostic or prognostic assays as described herein. Administration of a prophylactic agent can occur prior to the manifestation of symptoms characteristic of the differential marker protein expression, such that a disease or disorder is prevented or, alternatively, delayed in its progression. Depending on the type of marker aberrancy (e.g., increase or decrease in expression level), for example, a marker protein, marker protein agonist or marker protein antagonist agent can be used for treating the subject. The appropriate agent can be determined based on screening assays described herein. Examples of agents that modulate the FKBP marker can be immunosuppressants such as rapamycin, and analogues of rapamycin, such as CCI-779 and analogue described in U.S. Pat. No. 5,362,718, incorporated herein by reference, FK506, macolides of FK506 and rapamycin (Dumont, F. et al., "The Immunosuppressive Macrolides FK-506 and Rapamycin Act as Reciprocal Antagonists in Murine T Cells", *J. Immunol.* 144: 1418–1424 (1990), synthetic amnalogues of rapamycin and FK506 (R. S. Coleman et al., "Degradation and Manipulations of the Immunosuppressant FK506: Preparation of Potential Synthetic Intermediates," Heterocycles, 28, pp. 157–161 (1989) and U.S. Pat. No. 6,200,985, incorporated herein by reference.

6. Therapeutic Methods

Another aspect of the invention pertains to methods of modulating marker protein expression or activity for therapeutic purposes. Accordingly, in an exemplary embodiment, the modulatory method of the invention involves contacting a cell with a marker protein or agent that modulates one or more of the activities of a marker protein activity associated with the cell. An agent that modulates marker protein activity can be an agent as described herein, such as a nucleic acid or a protein, a naturally-occurring target molecule of a marker protein (e.g., a marker protein substrate), a marker protein antibody, a marker protein agonist or antagonist, a peptidomimetic of a marker protein agonist or antagonist, or other small molecule. In one embodiment, the agent stimulates one or more marker protein activities. Examples of such stimulatory agents include active marker protein and a nucleic acid molecule encoding marker protein that has been introduced into the cell. In another embodiment, the agent inhibits one or more marker protein activities. Examples of such inhibitory agents include anti-sense marker protein nucleic acid molecules, anti-marker protein antibodies, and marker protein inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a marker protein or nucleic acid molecule. In one embodiment, the method involves administering an agent (e.g., an agent identified by a screening assay described herein), or combination of agents that modulates (e.g., upregulates or downregulates) marker protein expression or activity. In another embodiment, the method involves administering a marker protein or nucleic acid molecule as therapy to compensate for reduced or aberrant marker protein expression or activity.

Stimulation of marker protein activity is desirable in situations in which marker protein is abnormally downregulated and/or in which increased marker protein activity is likely to have a beneficial effect. For example, stimulation of marker protein activity is desirable in situations in which a marker is downregulated and/or in which increased marker protein activity is likely to have a beneficial effect. Likewise, inhibition of marker protein activity is desirable in situations in which marker protein is abnormally upregulated and/or in which decreased marker protein activity is likely to have a beneficial effect.

7. Pharmacogenomics

The marker protein and nucleic acid molecules of the present invention, as well as agents, or modulators which have a stimulatory or inhibitory effect on marker protein activity (e.g., marker gene expression) as identified by a screening assay described herein can be administered to individuals to treat (prophylactically or therapeutically) marker-associated disorders (e.g., prostate cancer) associated with aberrant marker protein activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a marker molecule or marker modulator as well as tailoring the dosage and/or therapeutic regimen of treatment with a marker molecule or marker modulator.

Pharmacogenomics deals with clinically significant hereditary variations in the response to drugs due to altered drug disposition and abnormal action in affected persons. See, for example, Eichelbaum, M. et al. (1996) Clin. Exp. Pharmacol. Physiol. 23(10–11): 983–985 and Linder, M. W. et al. (1997) Clin. Chem. 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g. a "bi-allelic" gene marker map which consists of 60,000–100,000 polymorphic or variable sites on the human genome, each of which has two variants.) Such a high-resolution genetic map can be compared to a map of the genome of each of a statistically significant number of subjects taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a marker protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some subjects do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a marker molecule or marker modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a marker molecule or marker modulator, such as a modulator identified by one of the exemplary screening assays described herein.

This invention is further illustrated by the following examples which should not be construed as limiting. The contents of all references, patents and published patent applications cited throughout this application, are incorporated herein by reference.

EXAMPLES

Example 1

Identification and Characterization of Marker cDNA (i) Methods and Materials (a) Cell Cultures Human prostatic cancer cell lines LNCaP, DU-145, PC-3, and Tsu-prl were obtained from ATCC. LNCaP cancer cells were maintained in humidified atmosphere of 5% $CO_2$ in air in RPMI 1640 medium supplemented with 10% fetal calf serum (Life Technologies, Inc, Rockville, Md.), 3 mM L-glutamine, 100 µg/ml streptomycin and 100 units/ml penicillin. Other lines were maintained in DMEM containing 3 mM L-glutamine, 100 µg/ml streptomycin, 100 units/ml penicillin, and 10% FCS in humidified atmosphere of 5% $CO_2$. To examine the effects of steroids, cells were cultured in RPMI 1640 medium containing 5% FCS treated with dextran coated charcoal (Hyclone, Logan, Utah) for 24 hs before treatment. Cells were grown in the absence or presence of 10 nM DHT for 0, 2, 4, 6, 12, 24, 48, and 72 hs. They were collected and frozen at each time point. Two hundred µl of medium were collected from each flask for PSA assay.

(b) Cell Growth Assays

To verify the effect of DHT on the growth of LNCaP cells, cells at 3,000 cells/well were plated in 96-well plates for 24 hs before treatment with DHT. After 72 hs, MTT was added to each well and incubated at 37° C. for four hs. At the end of incubation, the supernatant was removed and 100 µl DMSO was added to each well to dissolve the cells. Plates were subsequently read in a plate reader at 570 nM.

(c) PSA ELISA

Quantification of PSA was performed using an ELISA. Briefly, a 96-well Nunc plate was coated with 100 µl of goat anti-PSA (1 µg/ml, Scripps laboratory, San Diego, Calif.) overnight at 40° C. The plate was washed with water three times and incubated with 100 µl of blocking buffer (PBS, 0.05% Tween 20, 1 µM EDTA, 0.25% BSA, and 0.05% $NaN_3$) for 1 h at room temperature. The plate was washed three times with water and incubated with 1:1 mixture of mouse anti-human PSA and Eu-labeled anti-mouse IgG (10 ng/antibody each/well for 1½ hs at RT). The plate was then washed four times with water. 100 µl of DELFIA® Enhancement Solution (PerkinElmer Wallac Inc (Norton, Ohio) was added to the plate was read using a Victor reader according to the manufacturer's instruction.

(d) RNA Extraction and Preparation

Total RNA was isolated from LNCaP cells using the Qiagen RNEASY® Midi Kit following the manufacturer's recommendations. For polyA (+) selection, the Promega POLYATRACT® kit was used according to manufacturer's procedures. Briefly, LNCaP cells were collected by centrifugation and the RNA isolated using the buffers and recommended procedures from the Qiagen kit. Following RNA extraction, all samples were frozen at −80° C. One microgram of poly A(+) RNA was used as template for synthesis of double-stranded cDNA using the GibcoBRL cDNA synthesis kit, with an oligo dT primer incorporating a T7 RNA polymerase promoter (10 minutes at 70° C. for priming, 65 minutes at 37° C. for first strand synthesis with Superscript II RT, followed by 150 min at 15.8° C. for second strand synthesis with E. coli ligase, E. coli polymerase, and RNAse H). The double-stranded cDNA was purified by Solid Phase Reversible Immobilization (SPRI) using the methods described by De Angelis et al. using Perseptives paramagnetic beads (See, De Angelis et al. (1995) Nuc. Acid Res. 23. 4742–4743.) Approximately 50 ng of double-stranded cDNA was used as template for in vitro transcription to make labeled cRNA (16 hours at 37° C., Epicenter T7 RNA polymerase, Enzo Laboratories bio-11-CTP, bio-11-UTP). The cRNA was purified by SPRI using paramagnetic beads (Bangs Laboratories), and total molar concentration was determined from the absorbance at 260. Prior to hybridization, 10 µg of labeled cRNA was fragmented randomly to an average length of approximately 50 bases by heating at 94° C. in 40 mM Tris-acetate pH 8.1, 100 mM potassium acetate, and 30 mM magnesium acetate, for 35 minutes.

For material made directly from cellular RNA, cytoplasmic RNA was extracted from cells by the method of Favaloro et al. ((1980) Methods Enzymol. 65: 718–749), and poly (A) RNA was isolated with an oligo dT selection step (Promega PolyAtract mRNA Isolation System IV, Madison, Wis.).

(e) Chip Hybridization and Analysis

Figure 2:
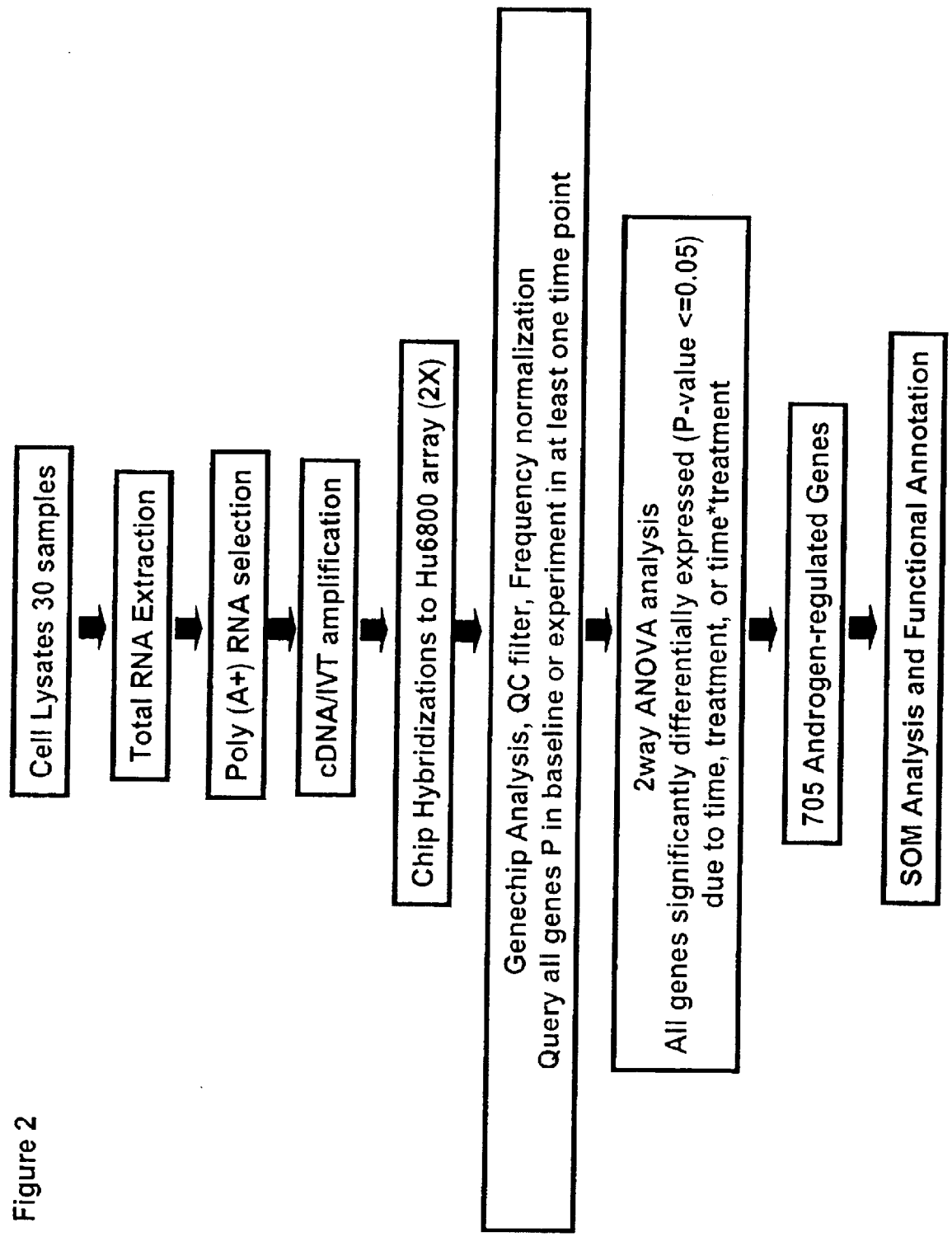
FIG. 2 is a flowchart demonstrating the procedure for RNA sample preparation, Affymetrix GENECHIP® hybridizations and analysis.

Affyinetrix GENECHIP® technology was used to monitor the expression of about 6000 full-length human genes in response to a natural androgen DHT in LNCaP cells. FIG. 2 illustrates the general scheme used for sample preparation, hybridization, and analysis. Hybridization cocktail was made using 10 µg of fragmented cRNA, 2×MES buffer with BSA, herring sperm DNA, control prokaryotic transcripts for internal control, and biotinylated control oligo 948 (for chip quality control). DEPC-water was added to bring the volume to 200 µl. Prior to hybridization, the hybridization cocktails were heated to 99° C. for 10 minutes, and then 37° C. for an additional 10 minutes before loading into Hu6800FL arrays (Affymetrix GENECHIP®. The Hu6800Fl array is comprised of 6800 known fill-length genes, about 250,000 25-mer oligonucleotide probes with 20 probe pairs per gene. Array hybridization proceeded overnight at 45° C. with 50 rpm. Following hybridization, the arrays were washed and stained using the manufacturer's recommendations and procedures. (Affymetrix Expression Analysis Technical Manual). Non-stringent wash buffer (20×SSPE, 1.0 ml of 10% Tween 20, and water) at 25° C., and stringent wash buffer (20×SSPE, 5M NaCl, 10% Tween 20, and water) at 50° C. were used for the wash steps. The arrays were then stained with strepavidin-conjugated phycoerythrin (SAPE, Molecular Probes), followed by biotinylated anti-strepavidin and a second round of SAPE for signal amplification at 25° C. Each stain step was done for 10 minutes. All arrays were then scanned using the HP Genearray Scanner and the resulting fluorescence emmisions were collected and quantified using Affymetrix Genechip sofiware. Within the software, the signal intensities for all the probes on each array were calculated from the scanned image, and the appropriate probe array algorithm was applied to determine the expression levels (average difference) for each gene. Average differences for all genes were converted into mRNA frequency estimates (in molecules per million) based on the standard spike-in control transcripts.

(f) Data Filtering and Statistics

Initial data was reduced by filtering for all genes called "present" by GENECHIP®. A two-way ANOVA was then performed on the replicate data for each of these genes in the statistical computing package S-plus. The potential effects of two experimental factors (treatment and time) and the interaction of both factors on the expression level were evaluated in the analysis of variance model, and the p-values for the main effects ($P_{treatment}$, $P_{time}$) and for the interaction ($P_{interact}$) were obtained. Only those genes that were statistically significant (p-value<=0.05) for the treatment factor and/or the interaction were considered for the time being. First, the average was taken for baseline and experimental replicate mRNA frequencies of the 705 genes that passed this p-value criterion. Average frequencies obtained for each gene were then standardized across all samples to have a mean of zero and a standard deviation of one. A modified version of the original self-organizing map (SOM) algorithm developed by Kohonen et at (Self-Organizing Maps, Second Extended Edition edition, Vol. 30. New York, 1997), created using the MATLAIB toolbox, was then applied to the standardized expression values to generate a 6 by 6 matrix of 36 clusters (Tamayo et al. (1999) *Proc. Natl. Acad. Sci. USA*. 96: 2907–2912). Several public databases such as Genecards and Swiss-Prot were used for gene annotation (See e.g., Rebhan et at. GeneCards: encyclopedia for genes, proteins and diseases. Weizmann Institute of Science, Bioinformatics Unit and Genome Center (Rehovot, Israel), 1997, and Appel et at. (1994). A new generation of information retrieval tools for biologists: *Trends Biochem. Sci.* 19:258–260.

(g) Quantitative TAQMAN®RT-PCR

The same total RNA samples used for the GENECHIP® experiments were analyzed using a TAQMAN® EZ RT-PCR kit (PE Applied Biosystems) to confirm gene expression changes. Total RNA samples were diluted to a concentration of 50 ng/ul and a total of 50 ng was used for each reaction. Primers and florescence probes for PSA and FKBP54 were designed using the Primer Express software and were chosen based upon the manufacturer's recommendations for primer selection. The primers used were of 100 uM concentration and were as follows: (a) PSA-F (forward primer) CGTGGCCAACCCCTGA (SEQ ID NO: 1), PSA-R (reverse primer) CTTGGCCTGGTCATTTCCAA (SEQ ID NO: 2), and PSA-P (probe) CACCCCTATCAAC-CCCCTATTGTAGTAAACTTGGA (SEQ ID NO: 3). (b) FKBP54-F (forward primer) CTGTGACAAGGCCCT-TGGA (SEQ ID NO: 4), FKBP54-R (reverse primer) CTGGGCTTCACCCCTCCTA (SEQ ID NO: 5), and FKBP54-P (probe) ACAAGCCTTTCTCATTGGCACT-GTCCA (SEQ ID NO: 6).

Samples were prepared using a reagent mix of manufacturer supplied RT-PCR components [(5× TAQMAN® EZ Buffer, manganese acetate (25 mM), dATP (10 mM), dCTP (10 mM), dGTP (10 mM) and dUTP (20 mM), rTth DNA polymerase (2.5 U/µl), AmpErase UNG (1 U/µl), primers (final concentration 1 µM) and RNA (50 ng)], following manufacturer's recommendations. In addition, GAPDH control samples for standard curve generation and subsequent quantitation of sample RNA was prepared. Primers and probe for GAPDH were included in the kit (GAPDH forward and reverse primers 10 µM, GAPDH probe 5 µM).

β-actin was also used for standard curve generation, and dilutions were made for both genes that ranged from $5 \times 10^6$ copies to $5 \times 10^1$ copies. The assay was performed on a Perkin-Elmer/Applied Biosystems 7700 Prism, and the PCR cycling parameters were chosen based on the manufacturer's recommendations. RNA of samples were normalized to GAPDH and β-actin and was quantified.

(h) Western Blot Analysis

For Western blot analysis, LNCaP cells were plated in 6-well plate at $1 \times 10^6$ cells/well in charcoal stripped serum containing medium. Cells were treated with 10 nM DHT and harvested at designated time. Cells were harvested in MPER reagent (Pierce, Rockford, Ill.) containing 400 mM NaCl. Protein was quantified by Bradford method (Bradford (1976) Anal. Bioch. 72: 248–254). 30 µg of protein was electrophoresed on a 12% SDS-PAGE gel and transferred to a PVDF membrane using a Bio Rad liquid transfer apparatus. The PVDF membrane was incubated in TBST (TBS with 0.1%Tween-20) with 3% milk for 15 minutes before the addition of the first antibody, rabbit anti-FKBP54 (Affinity Bioreagents, Inc). After overnight incubation, the PVDF membrane was washed 3 times with TBST and incubated with a second antibody, anti-rabbit-IgG coupled with horseradish peroxidase (Transduction Labs) for one hour. The PVDF membrane was then washed 3 times with TBST and protein was detected by using an enhanced chemiluminescence detection system (Pierce).

(i) Tissue Microarray Construction and Analysis

To investigate the presence of FKBP54 in solid tumors, tissue microarray analysis was performed on multiple human normal (i.e., control samples) and prostate diseased specimens (Clinomics, Inc.). Following fixation in 10% neutral buffered formalin, tissues were selected, trimmed, and placed in a processing cassette. The cassette was then placed in a processing basket on a Shandon Hypercenter™ tissue processor in which the tissues were exposed to a series of buffers over a 16 hour processing cycle (10% Neutral Buffered formalin, 70%, 95%, 100% ethanol, xylene, and melted paraffin embedding media). All steps were carried out under vacuum at 40° C. except for the paraffin steps which were at 58° C. Following processing, the tissues were removed from the cassettes and embedded in paraffin blocks. The resulting blocks were sectioned at 5 µm and mounted on glass slides. The slides were heated at 58° C. for 30 minutes prior to staining. Antibody α-FKBP54 (Affinity Bioreagents) was titered to a 1:150 dilution using DAKO® Antibody Diluent. Staining of test specimen was performed employing HIER in pH 6.0 citrate buffer with no pretreatment. Tissues were then stained using the Ventana ES® Automated Immunohistochemistry Stainer, involving the use of a standard indirect immunoperoxidase protocol with 3,3'-diaminobenzidine as a chromagen. Grading of the immunohistochemical staining was based on the intensity of the cytoplasmic staining of the epithelial components of both the tumor and the normal tissues. The strength of the staining was scored using a 1+ to 4+ scale, 1+ indicating faint staining and 4+ indicating strongest staining (appearing as dark brown staining). A score of 0 indicated no staining.

(j) Transient Transfection of COS Cells

To determine the effect of FKBP54 on the transcriptional activity of androgen receptor (AR), COS-1 cells were transiently transfected with a reporter construct containing androgen receptor response element along with an expression vector encoding FKBP54. COS-1 cells were plated in 6-well plates at a density of $2 \times 10^5$ cells per well in 2-ml pheno red-free DMEM containing 10% charcoal-stripped fetal bovine serum. The next morning, medium were replaced with 2-ml DMEM. Indicated amount of DNA in 100 μl of DMEM was mixed with 6 μl of PLUS reagent (Gibco) and incubated at room temperature while 4 μl of lipofectamine was mixed with 100 μl of DMEM. After 30 min of incubation, the two mixtures were combined together and added dropwise to each well. After incubation with DNA for 4 hours, 2 ml of phenol red-free DMEM containing 10% charcoal-stripped fetal bovine serum was added and cells treated with indicated chemicals for additional 24 hours before being harvested.

(k) Luciferase Assay

Luciferase activity was determined using Promega's STEADY GLO™ Luciferase Assay System. Briefly, after 24 hours of treatment, cells were harvested by scraping in 1 ml of PBS. 5 μg protein from each sample in a total of 100 μl PBS was mixed with 100 μl of STEADY GLO™ reagent (Promega), and luminescence was determined in a luminometer (Wallac, 1450 MicroBeth Counter) after 5 min.

(ii) Results

DHT Stimulates the Growth of LNCaP Cells and PSA Production

LNCaP cells are widely used as tumor models because they maintain responsiveness to androgen (Horoszewicz et al. (1983). *Cancer Res* 43: 1809–1818). For example, their ability to proliferate, to express differentiated secretory function, and to control processes such as lipid synthesis and accumulation, all remain androgen responsive. To ascertain whether LNCaP in the present culture conditions could be used to examine androgen-regulated genes, the response of LNCaP to androgen treatment was tested using the procedures described in sections (a-c). Cell growth and PSA production were studied.

FIG. 1A shows that the growth of LNCaP cells was stimulated by a natural androgen DHT in a dose-dependent manner. 10 nM DHT was chosen for the rest of the experiments because of its robust growth-stimulatory effect. PSA is a widely used prostate marker and was therefore tested in the present study prior to the microarray experiment. In response to DHT treatment, PSA production was increased in a dose-dependent manner (FIG. 1B). PSA signal was detected as early as 12 hs and the maximal level was observed at about 48 hs. These results demonstrated that LNCaP are responsive to DHT Genechip Hybridization and Analysis Affymetrix GENECHIP® technology was used to monitor the expression of about 6000 full-length human genes in response to a natural androgen DHT in LNCaP cells. FIG. 2 illustrates the general scheme used for sample preparation, hybridization, and analysis and the details of hybridization are described in section (e). To obtain reliable data, total RNA was prepared in duplicate from LNCaP cells treated or not with DHT for 0, 2, 4, 6, 12, 24, 48, and 72 hs as described in section (d). CRNAs were prepared and hybridized also in duplicate to Affymetrix chips. Therefore a set of biological replicates for a total of 30 samples were generated for each experiment to ensure reproducibility. Only those genes that were called "present" in either the baseline or the experiment in at least one time point and in either replicate passed the initial data reduction filter. Out of about 6000 genes represented on the chip, 4491 passed this initial filter (75%).

Statistical Analysis of Replicates

To assess reproducibility, the coefficient of variation (CV) to the mean frequencies of two replicates at each time point were compared. The results showed that across all genes, CV varied between 25 and 35% (data not shown). Based on the experimental design, a two-way analysis of variance (ANOVA) was used to determine the statistical significance of the ~4500 gene expression changes. The results based on a 95% significance level show that 200 genes were significant due to androgen treatment alone, 431 genes were significant due to an interaction of androgen treatment and time, and 74 genes were significant due to both the treatment factor and the interaction. Only androgen-regulated genes were identified, the 242 genes that were significantly modulated due to time alone were not considered.

Rapid Classification of Expression Profiles using Self-Organizing Maps

For rapid classification and to understand the potential function of candidate genes, expression profiles of the 705 genes found to be regulated by androgen and/or an interaction between androgen and time by ANOVA analysis were clustered using an adaptation of the self-organizing map (SOM) algorithm developed by Kohonen and Tamayo et al. (supra), mRNA frequencies of each gene were averaged within treatment/time subgroups, and the averaged frequencies over all subgroups were standardized such that the mean of the averaged frequency was set to zero, and the standard deviation equal to one. Based on standardized mRNA frequencies for each gene, a 6 by 6 matrix of 36 clusters was generated and visualized.

Identification of Androgen-Regulated Genes

Figure 3:
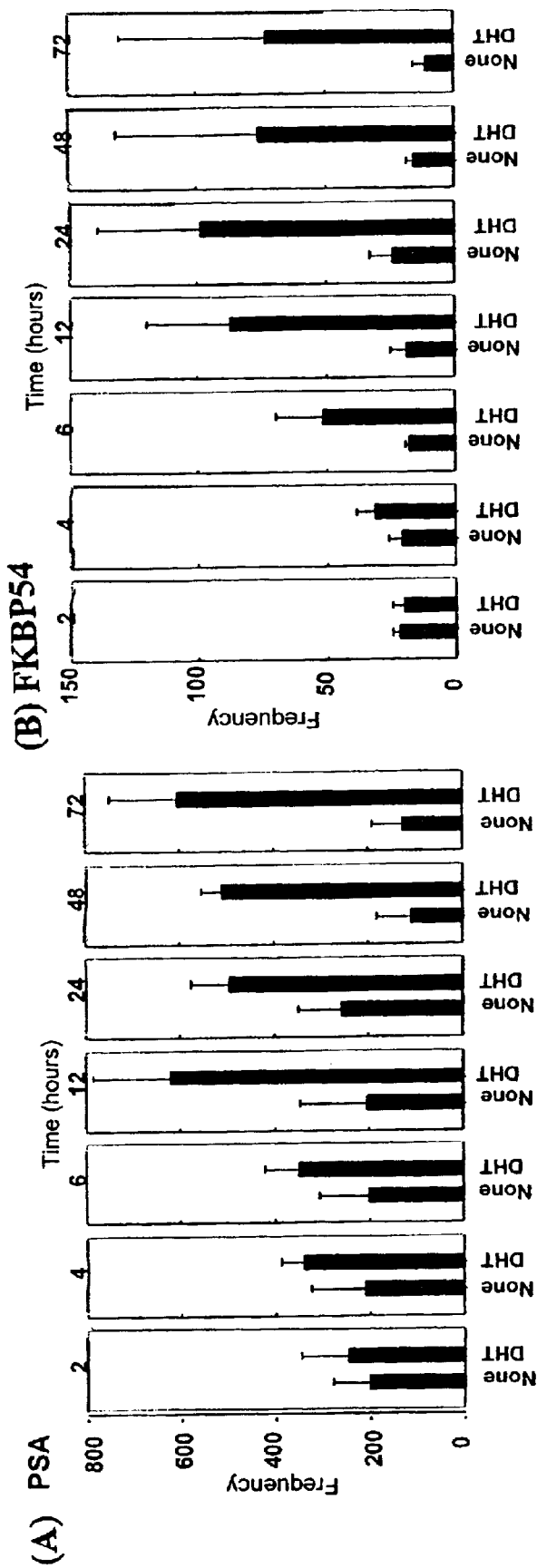
FIG. 3A is a bar chart depicting the expression profile of PSA in response to androgen treatment. The mRNA frequencies are plotted on the Y-axis, and the DHT androgen treated and untreated cells for each time point plotted on the X-axis.
FIG. 3B is a bar chart depicting the expression profile of FKBP54 in response to androgen treatment. The mRNA frequencies are plotted on the Y-axis, and the DHT androgen treated and untreated cells for each time point plotted on the X-axis.

For rapid classification and to understand the potential function of candidate genes, expression profiles of the 705 genes found to be regulated by androgen and/or an interaction between androgen and time by ANOVA analysis were clustered using an adaptation of the self-organizing map (SOM) algorithm developed by Kohonen and Tamayo et al. (Supra). The results showed that Cluster (1,1) included genes that shared a similar pattern of induced expression upon androgen treatment, while cluster (6, 6) included genes that had a pattern of repressed expression upon androgen treatment. Genes that are induced in response to androgen clustered together in Cluster (1,1) and included prostate specific antigen (PSA), the most widely used diagnostic marker for prostate cancer. Elevated PSA levels are often detected when cancer is present. In response to androgen treatment, PSA expression ($p_{treatment}$=0.0000, $p_{time}$=0.8682, $p_{interact}$=0.3282) increased 3-fold relative to control at 12 hours, and maintained its high expression through 72 hours where it was induced approximately 4-fold (FIG. 3A). Similarly, FKBP54 expression ($p_{treatment}$=0.0002, $p_{time}$=0.4369, $p_{interact}$=0.3818) in the control samples maintained a relatively low yet consistent pattern throughout the time-course. However, upon androgen-treatment, FKBP54 was rapidly induced 2-fold at 6 hours and peaked at 24 hours, where it was over-expressed approximately 4-fold relative to baseline (FIG. 3B).

Quantitative RT-PCR Analysis of RNA Samples

Figure 4:
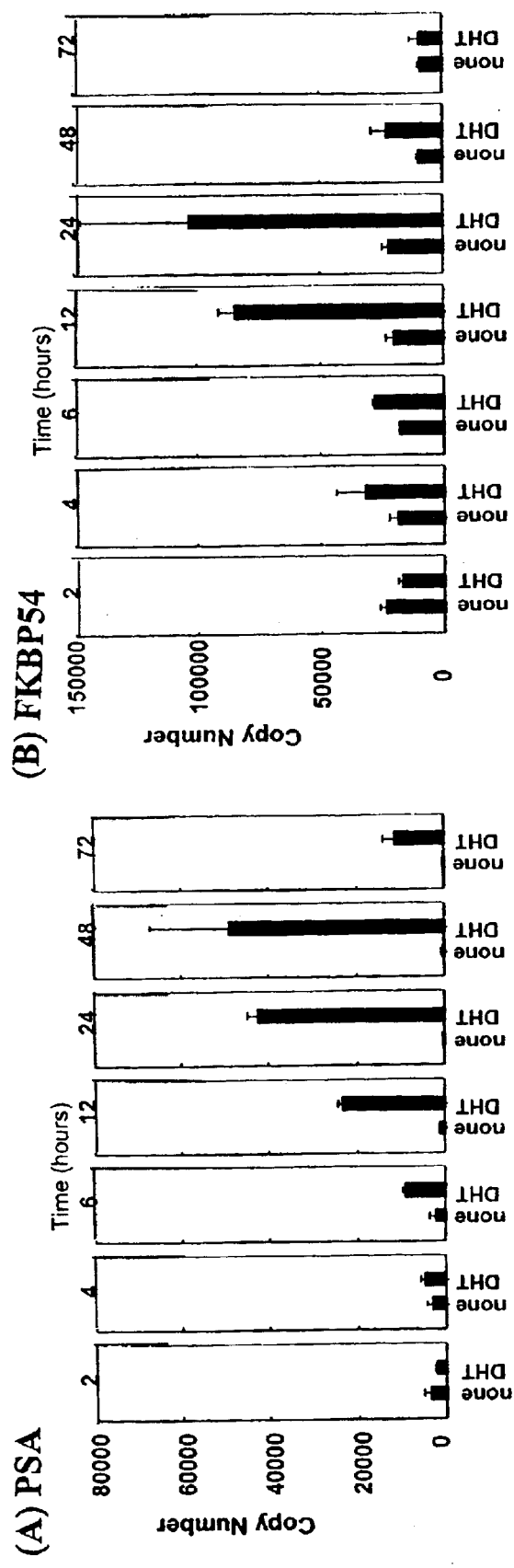
FIG. 4A is a bar chart demonstrating the quantitative RT-PCR analysis of PSA. Copy number is plotted on the Y-axis, and the DHT androgen treated and untreated cells for each time point plotted on the X-axis.
FIG. 4B is a bar chart demonstrating the quantitative RT-PCR analysis of FKBP54. Copy number is plotted on the Y-axis, and the DHT androgen treated and untreated cells for each time point plotted on the X-axis.

Quantitative RT-PCR was also used to confirm the gene expression changes from the GENECHIP® analysis as described in section (g). The results for qualitative RT-PCR are shown in FIGS. 4A and B, demonstrating the increase in RNA levels for PSA and FKBP54.

Production of FKBP51 was Regulated by Androgen

To demonstrate that the protein production of FKBP54 was regulated byandrogen, Western blot analysis was performed as described in section (h). The results show that DHT upregulated the FKB54 expression in a time-dependent manner (blot not shown). Similarly, a synthetic androgen, R1881 could also upregulate the FKBP54 expression (blot not shown), suggesting that the FKBP54 is regulated through androgen receptor. Interestingly, the protein level increased after 24 hs, which was 12 hs later than the transcript, suggesting that protein synthesis was required for the induction. The expression of FKBP54 was studied in several androgen-independent prostate cancer lines and was found present in all cell lines studied (Tsu-pr1, PC3, PC3-mm2, DU145, data not shown). The level of FKBP54 in hormone-independent lines was higher than non-treated LNCaP cells.

Table 1 summarizes band density values from the Western blot analysis. These results show that 24 hours post-DHT exposure, the level of FKBP54 expression increased approximately two-fold, and continued to increase to approximately 4-fold, 72 hours post-DHT exposure. With R1881 stimulation, there was an approximate 10-fold increase in FKBP54 expression 24 hours post-R1881 stimulation, and approximately 30-fold increase 72 hours post-R1881 exposure.

TABLE 1

Quantitative Expression Levels of FKBP54 with DHT and R1881 Stimulation

| Time (hr) | DHT Stimulation | R1881 Stimulation |
|---|---|---|
| 0 | 8.5 | 1.8 |
| 2 | 9.0 | 5.3 |
| 6 | 9.8 | 5.9 |
| 12 | 8.0 | 5.0 |
| 24 | 12.0 | 20.1 |
| 48 | 23.0 | 27.2 |
| 72 | 30.2 | 34.4 |

Additionally, some prostate cancer cells were identified as being sensitive to a rapamycin analog, CCI-779 (data not shown). Other rapamycin analogs as described in U.S. Pat. No. 5,362,718, incorporated herein by reference, may also be used. The presence of FKBP54 in cancer patients indicates that these patients may respond well to the CCI-779 treatment.

FKBP54 itself, may therefore also be a potential drug target for small molecule because it has intrinsic isomerase activity. Inhibitors of isomerase activity can be readily screened using a high throughput format using chymotrypsin as an isomer specific protease and monitoring the released 4-nitroanilline by absorbance measurements.

Immunohistochemistry Staining of Prostatic Adenocarcinoma with Anti-FKBP54

Immunohistochemistry staining of prostatic adenocarcinoma with anti-FKBP54 antibody of normal prostate and prostatic adenocarcinoma from a tissue microarray containing 50 specimens was performed as described in section (i). Visually, benign glands from normal samples (i.e., controls) generally did not express FKBP54 (data not shown) whereas regions with adenocarcinoma were generally positive with variable staining in both the nuclear and cytoplasmic epithelial elements in the 3 to 4+ range (data not shown).

FKBP54 Potentiates AR Transcriptional Activity

Figure 5:
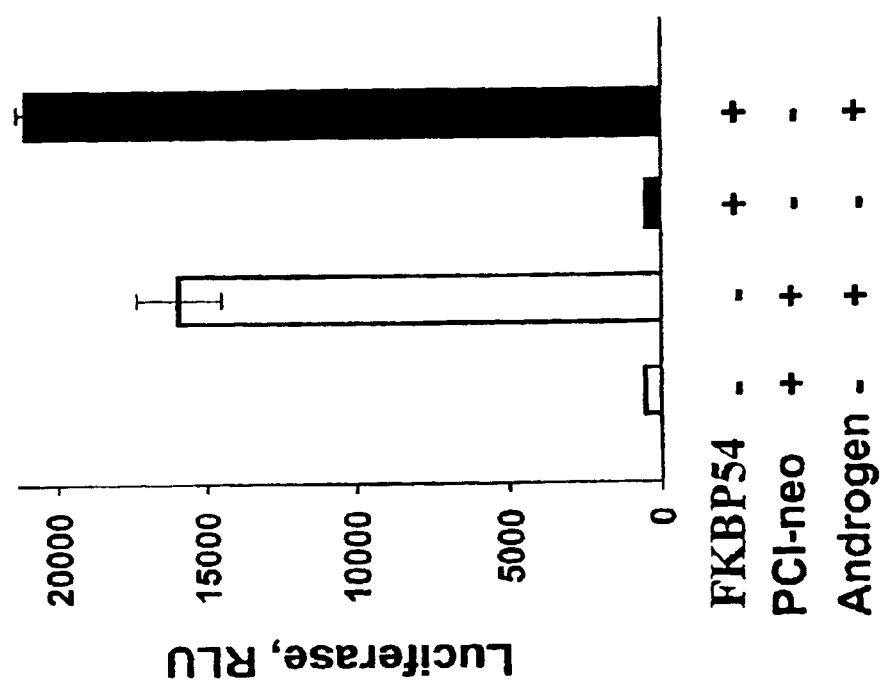
FIG. 5 is a bar chart demonstrating the transcriptional activation of androgen receptor (AR) by FKBP54 using COS-1 cells that were transiently transfected with GREe1bLuc reporter construct and 0.1 μg expression vector encoding FKBP54 (black bars) or empty vector (white bars). The COS-1 cells were treated with or without $10^{-9}$ M of the synthetic androgen, R1881 for 20 hrs. Bars represent the mean of at least three independent experiments±SD.

To determine the effect of FKBP54 on the transcriptional activity of androgen receptor (AR), COS-1 cells were transiently transfected with a reporter construct containing androgen receptor response element along with an expression vector encoding FKBP54 as described in section (j). As shown in FIG. 5, transfection of FKBP54 had no effect on the reporter activity but increased AR activity in the presence of androgen by more than 30%., demonstrating that FKBP54 potentiates AR transcriptional activity.

In summary, these results show that immunophilin FKBP54 was found to be androgen-regulated (by both DHT and R1881) and highly expressed in prostate tumor specimens relative to normal tissue. Moreover, tissue microarray results showed that the expression of FKBP54 correlated with Gleason score. The transient cotransfection study demonstrated that AR activation by androgen was enhanced by FKBP54, suggesting the functional role of FKBP54 in androgen receptor activation. The FKBP54 candidate ARGs may be useful for understanding the molecular mechanisms leading to the proliferation, differentiation, and function of the normal and diseased human prostate. Collectively, these results demonstrate that FKBP54 can be used as a diagnostic marker and is important for prostate tumor growth. The involvement of FKBP54 in prostate cancer as demonstrated herein, and modifying the expression of FKBP54 (up-regulated or downregulated) may provide a therapeutic effect in deterring the progression of prostate cancer. This modification may be by either existing agents, such as rapamycin, or novel agents identified by the screening methods of the invention.

Example 2

Screening for Compounds Useful for the Treatment of Prostate Cancer

The cDNA and protein sequence of FKBP54 is available in the public database Genbank with accession number U42031. The publications and sequence databases provide those skilled in the art with the genes needed to prepare the transfected cell lines useful in for the following screening assays.

Test compounds potentially useful for the treatment of prostate cancer can be identified by expressing FKBP54 in prostate cancer cells (e.g., WT LNCaP cells) which are stably transfected with a vector capable of expressing FKBP54 in the presence of tetracycline (Tet-on system, Clontech) The transfected WT LNCaP cells are cultured under suitable conditions (e.g., in T175 culture flasks in RPMI-1640 medium supplemented with 10%; fetal calf serum (FCS), 3 mM L-glutamine, 100 µg/ml streptomycin, and 100 units/ml penicillin. To examine the effects of steroids, cells can be cultured for 2 days in RPMI 1640 medium containing 5% FCS pretreated with dextrancoated charcoal (CT-FCS). The cells can be incubated in the presence a test compound with or without Tet and the growth rate of the cells is measured. A compound shows differential inhibitory activity in cells treated or not with Tet will be considered as a potential therapeutic compound that mediated its function through FKBP54 and therefore selected for further verification.

Example 3

Detection of FKBP Markers

To evaluate the role of FKBP markers, e.g., FKBP54 in cell growth and the effect in tumor inhibition, the growth rate of cells transfected with FKBP54 Tet-on expression vector, in the presence or absence of Tet will be determined. Altered growth will confirm the role of the FKBP54 in the regulation of tumor cell growth and assure the therapeutical value of immunophilin. The presence and expression levels of the FKBP54 marker can be assessed using standard molecular biology techniques as described in Sambrook et al, (1989) supra.

For the detection and quantitation of RNA species, the nucleic acids corresponding to the FKBP54 marker can be isolated and amplified. Pairs of primers that selectively hybridize to FKBP54 nucleic acid can be designed based on the nucleotide sequence of this marker, which are available from Genbank, accession number U42031. The primers can be contacted with the isolated nucleic acid under conditions that allow selective hybridization. Once hybridized, the nucleic acid:primer complex can be contacted with one or more enzymes that facilitate template-dependent nucleic acid synthesis using PCR amplification. The amplified product can be detected, for example by gel electrophoresis and visualization with ethidium bromide under UV light. Alternatively, if the amplification products can be integrally labeled with radio- or fluorometrically-labeled nucleotides, the amplification products can then be exposed to x-ray film or visualized under the appropriate stimulating spectra, following separation.

Other methods for detecting the presence and expression levels of the FKBP54 marker include detecting the FKBP54 marker protein by an ELISA immunodetection assay. For example, by using anti-FKBP54 antibodies to detect the presence of the FKBP54 marker expressed in a cell sample. Anti-FKBP54 antibodies can be immobilized onto a selected surface exhibiting protein affinity, such as a well in a polystyrene microtiter plate. Then, a cell sample suspected of containing the FKBP54 marker, can be added to the wells. After binding and washing to remove non-specifically bound immunocomplexes, the bound antibody may be detected. Detection can be achieved by the addition of a second antibody specific for a different region of the FKBP54 marker protein, that is linked to a detectable label.

Example 4

Detection of FKBP Markers in Solid Tumors

To determine whether FKBP, e.g., FKBP54 was effected at different stages of tumor growth, RNA can be isolated from normal prostate glands and prostate tumors with different Gleason grades. Solid tumors were scored using the Gleason scoring system (See e.g., Bostwick (1994) *Amer. J. Clin. Path.* 102: S38–56, incorporated herein by reference). The total RNA can be extracted and be examined for the level of expression of FKBP54 in these different tumor stages using the affymetrix microarrays, as described in Example 1.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method of assessing whether a human subject is afflicted with prostate cancer, the method comprising comparing:
   a) the level of expression of FKBP54 in a sample from a human subject, and
   b) the normal level of expression of FKBP54 in a control sample,
   wherein a significant increase in the level of expression of in the sample from the subject compared to the normal level is an indication that the human subject is afflicted with prostate cancer.

2. The method of claim 1, wherein the sample comprises cells obtained from the subject.

3. The method of claim 2, wherein the cells are collected from the prostate gland.

4. The method of claim 2, wherein the cells are collected from blood.

5. The method of claim 1, wherein the level of expression in the sample differs from the normal level of expression in a in a subject not afflicted with prostate cancer by a factor of at least about 2.

6. The method of claim 1, wherein the level of expression in the sample differs from the normal level of expression in a subject not afflicted with prostate cancer by a factor of at least about 3.

7. The method of claim 1, wherein the level of expression in the sample is assessed by detecting the presence in the sample of FKBP54 protein.

8. The method of claim 7, wherein the presence of the protein is detected using a reagent which specifically binds with the protein.

9. The method of claim 8, wherein the reagent is selected from the group consisting of an antibody, an antibody derivative, and an antibody fragment.

10. The method of claim 1, wherein the level of expression in the sample is assessed by detecting the presence in the sample of a transcribed polynucleotide or portion thereof.

11. The method of claim 10, wherein the transcribed polynucleotide is an mRNA.

12. The method of claim 10, wherein the transcribed polynucleotide is a cDNA.

13. The method of claim 10, wherein the detecting further comprises amplifying the transcribed polynucleotide or portion thereof.

14. A method for monitoring the progression of prostate cancer in a human subject, the method comprising:
   a) detecting in a subject sample at a first point in time, the expression of FKBP54;
   b) repeating step a) at a subsequent point in time; and
   c) comparing the level of expression detected in steps a) and b), and therefrom monitoring the progression of prostate cancer in the human subject, wherein an increase in the expression of the FKBP54 is an indication of prostate cancer progression in the human subject.

15. The method of claim 14, wherein the sample comprises cells obtained from the subject.

16. The method of claim 15, wherein the cells are collected from the prostate gland.

17. The method of claim 15, wherein the cells are collected from blood.

* * * * *